US012241904B2

(12) United States Patent
Moriura et al.

(10) Patent No.: US 12,241,904 B2
(45) Date of Patent: Mar. 4, 2025

(54) DISPLAY METHOD, SAMPLE ANALYZER, AND RECORDING MEDIUM

(71) Applicant: SYSMEX CORPORATION, Kobe (JP)

(72) Inventors: Kazuma Moriura, Kobe (JP); Hiroshi Kurono, Kobe (JP); Akihito Kato, Kobe (JP)

(73) Assignee: SUSMEX CORPORATION, Kobe (JP)

( * ) Notice: Subject to any disclaimer, the term of this patent is extended or adjusted under 35 U.S.C. 154(b) by 0 days.

(21) Appl. No.: 16/581,808

(22) Filed: Sep. 25, 2019

(65) Prior Publication Data

US 2020/0103429 A1 Apr. 2, 2020

(30) Foreign Application Priority Data

Sep. 28, 2018 (JP) .................. 2018-185947

(51) Int. Cl.
*G01N 35/00* (2006.01)
*G01N 33/86* (2006.01)
(Continued)

(52) U.S. Cl.
CPC ....... *G01N 35/00722* (2013.01); *G01N 33/86* (2013.01); *G06F 3/0482* (2013.01); *G06F 3/0483* (2013.01); *G01N 2035/0091* (2013.01)

(58) Field of Classification Search
CPC ... G01N 35/00722; G01N 2035/00891; G01N 2035/0091; G01N 33/4925; G01N 15/1459; G01N 15/147; G01N 2015/1486; G01N 2035/009; G01N 35/00871; G01N 33/86; G01N 33/50; H04N 1/00423; G06F 3/048
(Continued)

(56) References Cited

U.S. PATENT DOCUMENTS 11,543,422 B2 * 1/2023 Sugiyama ........ G01N 35/00732
2006/0259265 A1 11/2006 Mishima et al.
(Continued)

FOREIGN PATENT DOCUMENTS

CN 101393226 A 3/2009
CN 104508490 A 4/2015
(Continued)

OTHER PUBLICATIONS

Japanese Office Action (JPOA) issued on Feb. 12, 2020 in a counterpart Japanese patent application.
(Continued)

*Primary Examiner* — Patrick F Riegler
(74) *Attorney, Agent, or Firm* — METROLEX IP LAW GROUP, PLLC; Robert L. Scott, Esq

(57) ABSTRACT

A method according to one or more aspects may be for displaying measurement results of measurement items by a sample analyzer. The method may include displaying each of the measurement items selectably on a display unit, and displaying a notification concerning any of the measurement results in association with the corresponding measurement item on the display unit; and in response to selection of at least one of the measurement items, displaying the measurement result of the selected at least one of the measurement items on the display unit.

12 Claims, 20 Drawing Sheets

(51) Int. Cl.
　　　*G06F 3/0482*　　(2013.01)
　　　*G06F 3/0483*　　(2013.01)
(58) Field of Classification Search
　　　USPC ......................................................... 715/777
　　　See application file for complete search history.

(56) References Cited

U.S. PATENT DOCUMENTS

| | | | | |
|---|---|---|---|---|
| 2006/0263905 | A1* | 11/2006 | Mishima | G01N 33/56972 |
| | | | | 436/520 |
| 2006/0265173 | A1* | 11/2006 | Mishima | G01N 15/147 |
| | | | | 702/118 |
| 2007/0016440 | A1* | 1/2007 | Stroup | G06Q 10/10 |
| | | | | 705/2 |
| 2007/0078631 | A1* | 4/2007 | Ariyoshi | G16H 40/63 |
| | | | | 702/189 |
| 2008/0071503 | A1* | 3/2008 | Fujita | G01N 35/00722 |
| | | | | 702/188 |
| 2009/0074618 | A1 | 3/2009 | Mizumoto et al. | |
| 2009/0082984 | A1* | 3/2009 | Wakamiya | G06F 11/0769 |
| | | | | 702/85 |
| 2009/0215184 | A1* | 8/2009 | Wakamiya | G01N 35/00623 |
| | | | | 422/64 |
| 2010/0114501 | A1* | 5/2010 | Kondou | B01L 3/527 |
| | | | | 702/22 |
| 2012/0160039 | A1* | 6/2012 | Tatsutani | G01N 35/0092 |
| | | | | 73/863.91 |
| 2012/0253693 | A1* | 10/2012 | Inomata | G01N 35/00663 |
| | | | | 702/31 |
| 2013/0011298 | A1* | 1/2013 | Itou | G01N 35/00623 |
| | | | | 422/73 |
| 2013/0160533 | A1* | 6/2013 | Fukuma | G01N 35/00584 |
| | | | | 73/863.01 |
| 2014/0250339 | A1* | 9/2014 | Ishii | G01N 35/00623 |
| | | | | 714/57 |
| 2015/0185208 | A1* | 7/2015 | Pinkowitz | G01N 35/00871 |
| | | | | 435/288.7 |
| 2015/0276705 | A1* | 10/2015 | Maeda | G06F 9/542 |
| | | | | 702/19 |
| 2016/0274133 | A1* | 9/2016 | Yabutani | G01N 33/86 |
| 2018/0109955 | A1* | 4/2018 | Nixon | H04L 43/10 |
| 2018/0349564 | A1* | 12/2018 | Takemoto | G06F 3/1208 |
| 2020/0103429 | A1* | 4/2020 | Moriura | G06F 3/0482 |
| 2020/0174028 | A1* | 6/2020 | Kurono | G01D 3/00 |
| 2022/0043702 | A1* | 2/2022 | Haines | G06F 11/0772 |

FOREIGN PATENT DOCUMENTS

| | | |
|---|---|---|
| JP | 2010-256260 A | 11/2010 |
| JP | 2013-090264 A | 5/2013 |
| JP | 2013-167561 A | 8/2013 |
| JP | 2013-238618 A | 11/2013 |
| JP | 2014-089129 A | 5/2014 |
| JP | 2015-127646 A | 7/2015 |
| JP | 2015-179022 A | 10/2015 |
| JP | 2017-129593 A | 7/2017 |
| WO | 2015/098473 A1 | 7/2015 |

OTHER PUBLICATIONS

Extended European search report (EESR) issued on Mar. 10, 2020, 2020 in a counterpart European patent application.
Japanese Office Action issued on Oct. 20, 2020 for the counterpart Japanese patent application, with English translation.
Communication pursuant to Article 94(3) EPC issued on May 25, 2021 for the counterpart European patent application.
Office Action issued on May 26, 2020 in a counterpart Japanese patent application.
Communication pursuant to Article 94(3) EPC issued on Jan. 12, 2023 in a counterpart European patent application.
Office Action (CNOA) issued on Oct. 11, 2023 in a counterpart Chinese patent application, with English translation.
CNOA issued on May 17, 2024 in a counterpart Chinese patent application.

* cited by examiner

| STATE | SAMPLE NUMBER | RACK NUMBER POSITION | MEASURE DATE STARTDATE | START TIME | END TIME | PT THS | APTT | Fbg | DD | AT3 | CROSS MIXING | V |
|---|---|---|---|---|---|---|---|---|---|---|---|---|
| Complete | SHP_05025051 | A12345-06 | 2016/07/18 | 10:00 | 11:00 | | | | | | | |
| Complete | 12345678_123456 | 123456-02 | 2016/07/19 | 20:00 | 20:10 | 0123456 | 0123456 | 0123456 | 0123456 | | | |
| Review | 12345678901:2343 | 123456-03 | 2016/07/19 | 20:00 | 20:10 | 0123456 | 0123456 | 0123456 | 0123456 | | | |
| Review | 12345678901:2344 | 123456-04 | 2016/07/18 | 20:00 | 20:10 | ****** | ****** | ****** | ****** | | | |
| Review | 12345678901:2345 | 123456-05 | 2016/07/18 | 20:00 | 20:10 | ****** | ****** | ****** | ****** | | | |
| On Hold | 12345678901:2346 | 123456-06 | 2016/07/18 | 20:00 | | | | | | | | |
| Processing | 12345678901:2347 | 123456-07 | 2016/07/18 | 20:00 | | | | | | | | |
| Processing | 2345678_0123456 | 123456-08 | 2016/07/18 | 20:00 | | | | | | | | |
| Processing | 2345678_0123457 | 123456-09 | 2016/07/18 | 20:00 | | | | | | | | |
| Processing | 345678_01234510 | 123456-10 | 2016/07/18 | 20:00 | | | | | | | | |
| Processing R | 45678_012345211 | 123456-11 | 2016/07/18 | 20:00 | | | | | | | | |
| Processing | 2345678_0123452 | 123456-12 | 2016/07/18 | 20:00 | | | | | | | | |
| Processing | 2345678_0123453 | 123456-13 | 2016/07/18 | 20:00 | | | | | | | | |
| Processing R | 45678_012345214 | 123456-14 | 2016/07/18 | 20:00 | | | | | | | | |
| Pending | 45678_012345215 | 123456-15 | 2016/07/18 | 20:00 | | | | | | | | |
| Pending | 45678_012345216 | 123456-16 | 2016/07/18 | 20:00 | | | | | | | | |
| Pending | 45678_012345217 | 123456-17 | 2016/07/18 | 20:00 | | | | | | | | |
| Pending | 45678_012345218 | 123456-18 | 2016/07/18 | 20:00 | | | | | | | | |
| Pending | 45678_012345219 | 123456-19 | 2016/07/18 | 20:00 | | | | | | | | |
| Error | 45678_012345220 | 123456-20 | 2016/07/18 | 20:01 | | | | | | | | |

| ITEM | NUMBER OF TIMES | DILUTION RATE | MEASUREMENT SITE | | |
|---|---|---|---|---|---|
| PT sec | 1 | R1-10 | 1/1 | ****** | |
| PT % | | | 1/1 | 123.5 | |
| PT R | | | 1/1 | 123.4 | |
| APTT | | | | | |
| Fbg | | | | | |

Early Reaction Error: Start Angle 2

⇩ DISPLAY MEASUREMENT RESULT

FIG. 13

| STATE | ID | PATIENT NAME | DATE |
|---|---|---|---|
| | 704312456 | HANAKO KADAN | 2011/04/01 |
| RETEST RECOMMENDED | 230712001 | TARO HACHIUE | 2011/04/01 |
| | 552171002 | JIRO BONSAI | 2011/04/01 |
| | 712100322 | HANAMI SEIKA | 2011/04/01 |

| ITEM NAME | |
|---|---|
| CPK | 220 |
| CPK-MB | |
| LDH | 462 |
| TP | 7.7 |

RETEST RECOMMENDATION COMMENT

CARDIOMYOPATHY CHECK

REQUEST   CANCEL

RETEST RECOMMENDED   SAMPLE ATTRIBUTE

Tabs: ROUTINE OPERATION | REAGENT MANAGEMENT | CALIBRATION | ACCURACY MANAGEMENT | UTILITY

ITEM SELECTION | MEASUREMENT RESULT

Buttons: STOP, SAMPLE STOP, ALARM, START

DISPLAY METHOD, SAMPLE ANALYZER, AND RECORDING MEDIUM

CROSS REFERENCE TO RELATED APPLICATIONS

This application claims priority from to prior Japanese Patent Application No. 2018-185947 filed with the Japan Patent Office on Sep. 28, 2018, the entire contents of which are incorporated herein by reference.

BACKGROUND

The disclosure relates to, for example, a method of displaying a measurement result in a sample analyzer, and so on.

There have been known sample analyzers that perform measurement of measurement items on a sample and display measurement results. Among such sample analyzers, there is a sample analyzer characterized in a screen configuration in order to prevent a screen that displays a list of measurement results from becoming complicated along with an increase of measurement items. For example, Japanese Patent Application Publication No. 2013-167561 ("Patent Literature 1") discloses a screen configuration on which an operator can divide measurement items into groups and create a heading for each of the groups (see FIG. 12).

As the aforementioned display screen that displays the list of the measurement results, there is also a display screen that displays notifications concerning a sample and test items. For example, Japanese Patent Application Publication No. 2010-256260 ("Patent Literature 2") discloses a screen configuration for highlighting a notification that a retest is recommended for a specific sample (A2) and highlighting a notification that additional measurement of a specific measurement item is recommended for the sample (A3) (see FIG. 13).

However, in the conventional screen configuration explained above, there is a problem in that, when an information amount displayed on the screen increases, it is difficult to recognize notifications presented to the operator. For example, in the screen configuration illustrated in FIG. 13, information on a patient and information on the measurement items are displayed on the same screen. Therefore, the highlighted regions (A2 and A3) are narrowed and, as a result, recognizability is deteriorated.

In addition, the recognizability is also deteriorated due to an increase in the number of measurement items. For example, in the screen configuration illustrated in FIG. 12, even if headings A1 are highlighted, an increase in the number of measurement items makes it likely that the highlighted headings A1 cannot be recognized unless a scroll region S is operated (note that Patent Literature 1 itself does not disclose a configuration for "highlighting the headings A1"). In the screen configuration illustrated in FIG. 13, when the number of samples and the number of measurement items increase, it is sometimes necessary to operate the scroll region S in order to find the highlighted parts A2 and A3. Therefore, it is likely that a time is required for the operator to recognize the highlighted parts A2 and A3.

In this way, the screen configuration for displaying the measurement items on a row-by-row basis has a tendency that, as the number of rows increases, the operator needs to operate the scroll region in order to find a notification concerning the measurement items, and therefore has a tendency that a time is required for the operator to recognize the notification.

One or more aspects have been devised in order to solve the problems described above and may aim to provide a method of displaying a measurement result by a sample analyzer with which a notification concerning a measurement result can be easily recognized.

SUMMARY

A method according to one or more aspects may be for displaying measurement results of measurement items by a sample analyzer. The method may include displaying each of the measurement items selectably on a display unit, and displaying a notification concerning any of the measurement results in association with the corresponding measurement item on the display unit; and in response to selection of at least one of the measurement items, displaying the measurement result of the selected at least one of the measurement items on the display unit.

A sample analyzer according to one or more aspects may display measurement results of measurement items. The sample analyzer may including a controller and a display unit. The controller may display each of the measurement items selectably on the display unit, and display a notification concerning any of the measurement results in association with the corresponding measurement item on the display unit. The controller, in response to selection of at least one of the measurement items, may display the measurement result of the selected at least one of the measurement items on the display unit.

A non-transitory computer-readable storage medium storing a computer program according to one or more aspects may be used in a sample analyzer that displays measurement results of measurement items. The computer program, when read and executed, may cause the sample analyzer to perform operations including: displaying each of the measurement items selectably on a display unit, and displaying a notification concerning any of the measurement results in association with the corresponding measurement item on the display unit; and in response to selection of at least one of the measurement items, displaying the measurement result of the selected at least one of the measurement items on the display unit.

BRIEF DESCRIPTION OF DRAWINGS

FIG. 4 is a diagram illustrating a screen configuration example of a job list display screen;

FIG. 8A and FIG. 8B are diagrams each illustrating a measurement result display screen in a second embodiment: FIG. 8A illustrating a case in which a tab, on which an error notification mark is displayed, is present; and FIG. 8B illustrating a case in which the tab, on which the error notification mark is displayed, is absent;

FIG. 11A to FIG. 11D are transition diagrams each illustrating a display screen in an assumed scenario in which an embodiment is usefully used;

FIG. 13 is a diagram illustrating a display screen for a measurement result in related art.

DETAILED DESCRIPTION

Figure 1:
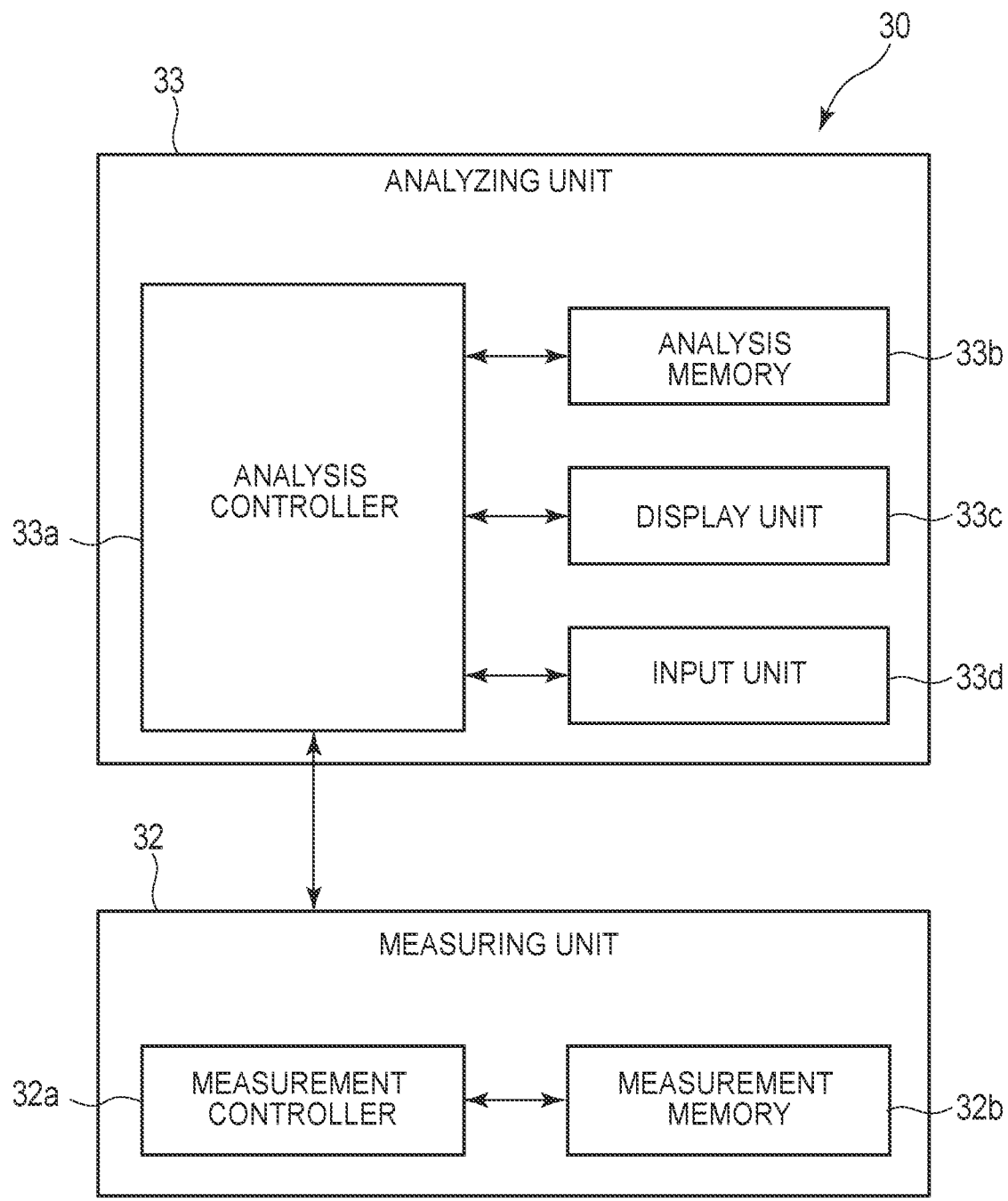
FIG. 1 is a block diagram illustrating a main part configuration of a sample analyzer according to an embodiment.

In order to solve the problems described above, a display method according to one or more aspects is a method of displaying measurement results of measurement items by a sample analyzer (30), the display method including: a notification displaying step of selectably, or as selectable or in a selectable manner, displaying each of the measurement items on a display unit (33*c*) and displaying a notification concerning the measurement result in association with the measurement item on the display unit (33*c*); and a measurement-result displaying step of displaying, in response to selection of at least one of the measurement items, a measurement result of the selected measurement item on the display unit (33*c*).

With the configuration explained above, on a display screen for causing an operator of the sample analyzer (30) to select a measurement item in order to display a measurement result, a notification concerning a certain measurement result is displayed on the display unit (33*c*) in association with the measurement item. Accordingly, the operator of the sample analyzer (30) can recognize, in a stage for selecting the measurement item, that the notification concerning the measurement result is present.

Note that an elapse of time is not always necessary between the measurement-result displaying step and the notification displaying step. For example, the measurement-result displaying step and the notification displaying step may be simultaneously performed.

In the notification displaying step, the measurement items may be displayed such that each of the measurement items is selectable by or with a tab (710) and the notification concerning the measurement result may be displayed on the tab (710).

With the configuration explained above, on a measurement result display screen (700), the notification concerning the measurement result is displayed in a region of the tab (710). That is, the notification concerning the measurement result is displayed on the tab (710) itself rather than in a region where display changes along with switching of the tab (710). Accordingly, the operator of the sample analyzer (30) can easily recognize a tab (710*c*) on which the notification concerning the measurement result is displayed.

Examples of the notification concerning the measurement result include a notification of an error concerning the measurement results and a notification of measurement completion.

For example, when measurement items are displayed by tabs, examples of a method of displaying the notification concerning the measurement result include displaying some sign (!, *, ⨯, ★, or the like; an error notification mark 715), changing heading characters of the tab (710*c*) (bold characters, colored characters, large characters, or the like), and coloring a background of the tab (710*c*). The method of displaying the notification concerning the measurement result may be varied or different according to content and importance of the notification.

The measurement items may be measurement items of a blood coagulation analysis.

Figure 12:
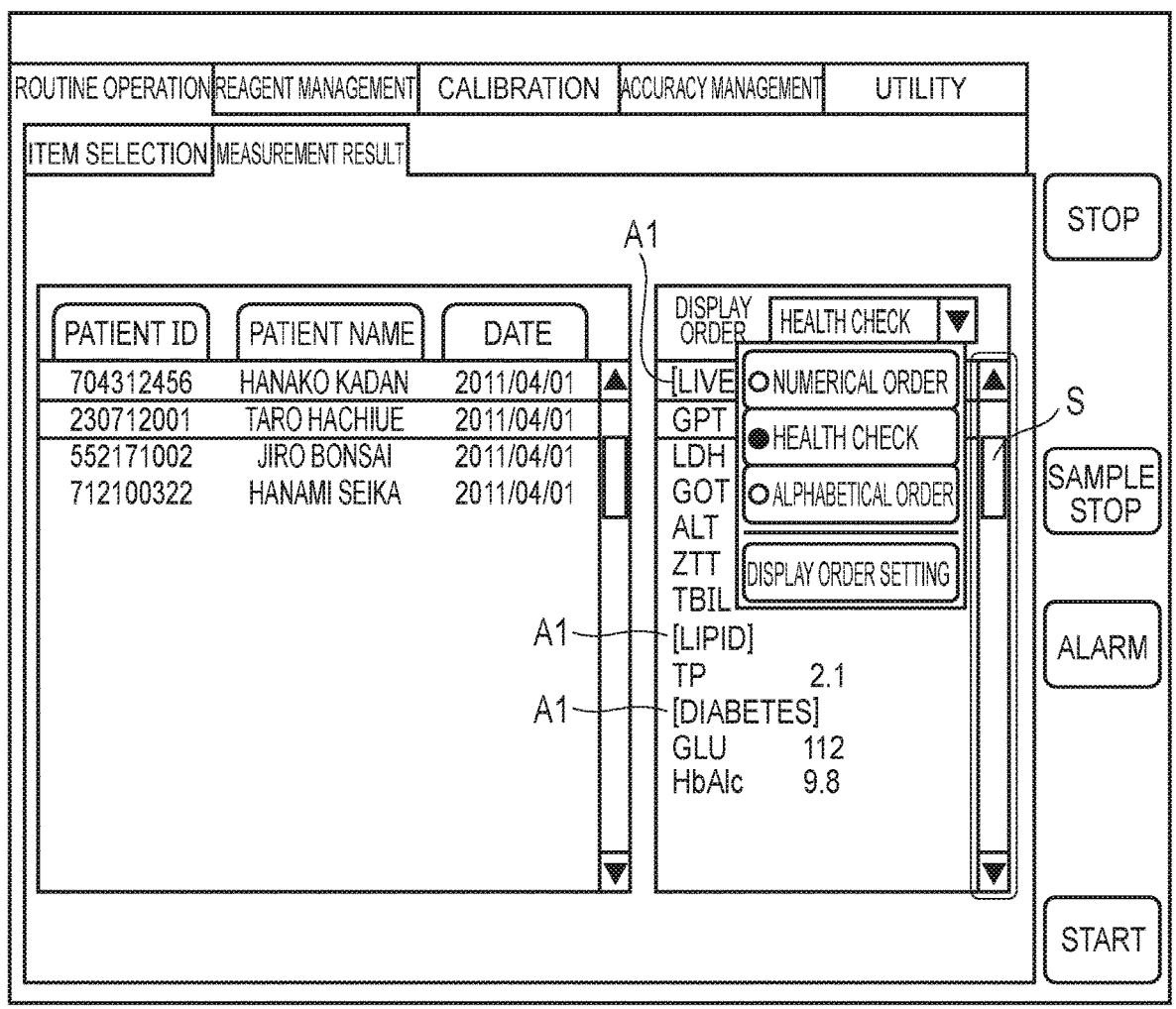
FIG. 12 is a diagram illustrating a display screen for a measurement result in related art.

For example, Patent Literatures 1 and 2 are based on a clinical test for samples of blood and urine. Such a test generally has a large number of measurement items. Therefore, it is a general practice to display the measurement items for each one row and provide the scroll region S illustrated in FIG. 12. However, the inventors have found that, for example, as in the blood coagulation analysis, in the case of a test in which the number of measurement items is relatively small, it is possible to improve recognizability of the notification concerning the measurement result by displaying the notification in association with the measurement results.

With the configuration explained above, measurement items of the blood coagulation analysis are displayed on the measurement result display screen (700). The number of measurement items of the blood coagulation analysis tends to be smaller than the numbers of measurement items of other clinical tests. For example, in an initial test for a subject suspected to suffer from hemophilia, usually, three items of the number of platelets, a prothrombin time, and an activated partial thromboplastin time (APTT) are measured by the blood coagulation analysis. Therefore, if the display method according to one or more aspects is applied to the blood coagulation analysis and the measurement items are displayed by tabs, it is less likely that the number of tabs displayed in the measurement-result displaying step is excessively large. Therefore, a display method of displaying a tab for each of measurement items is particularly suitable for the display of the measurement results of the blood coagulation analysis.

In the measurement-result displaying step, a graph related to the measurement result may be displayed together with the measurement results.

With the configuration explained above, in the measurement-result displaying step, the graph related to the measurement result is displayed on the measurement result display screen (700) together with the measurement results. In general, a wide display region is necessary for the display of the graph. With a display method of displaying a tab for each of measurement items and displaying a measurement result of a measurement item associated with a selected tab, since an amount of measurement results that should be displayed on one screen is reduced, it is easy to secure a display region necessary for the display of the graph. As a result, it is possible to provide a graph with high visibility to the operator of the sample analyzer (30).

The graph may be a graph obtained from measurement data or the measurement results.

Examples of such a graph include a scattergram, a coagulation waveform, and a calibration curve. These graphs are graphs having high importance in an analysis of a sample and particularly desired to be displayed on the measurement result display screen (700).

The measurement items may be measurement items of a blood coagulation analysis, and the graph may be a coagulation waveform, or a waveform in coagulation of the blood coagulation analysis.

In order to interpret a measurement result of the blood coagulation analysis, the coagulation waveform is extremely important. For example, when occurrence of an early reaction error (Start Angle, Early %, Slow Reaction, or the like) is notified (an error of a measurement result is notified), in order to determine whether the measurement result is appropriate, the coagulation waveform is referred to. It is desirable to adopt, such that a display region for a coagulation waveform with high visibility can be secured, the display method of displaying a tab for each of measurement items and displaying a measurement result of a measurement item associated with a selected tab.

The graph may be a calibration curve.

The calibration curve is important information for guaranteeing reliability of the measurement results of the measurement items. Accordingly, it is also desirable to display the calibration curve on the measurement result display screen (700) for the measurement items. Therefore, it is particularly desirable to adopt, such that a display region for a calibration curve with high visibility can be secured, the display method of displaying a tab for each of measurement items and displaying a measurement result of a measurement item associated with a selected tab.

The notification may be a notification for calling attention of an operator of the sample analyzer (30).

With the configuration explained above, attention of the operator of the sample analyzer (30) is called by the notification displayed in association with the measurement items in the notification displaying step. For example, when the measurement item is displayed by the tab (710), the operator of the sample analyzer (30) can immediately recognize in which measurement item a matter that should be paid attention is present, even without selecting the tab (710c) on which the notification is displayed. Thereafter, the operator of the sample analyzer (30) can select the tab (710c) on which the notification is displayed and confirm details of the matter that should be paid attention.

Examples of the notification for calling attention include a notification of an error concerning the measurement results and a notification of measurement completion of an emergency sample.

The notification may be a notification of an error concerning the measurement results.

The notification of the error concerning the measurement results is a notification having particularly high emergency among notifications concerning the measurement results. With the configuration explained above, for example, when the measurement item is displayed by the tab (710), even if the operator of the sample analyzer (30) does not select the tab (710c) on which the notification of the error is displayed, the operator of the sample analyzer (30) can immediately recognize in which measurement item the error occurs. Thereafter, the operator of the sample analyzer (30) can select the tab (710c) on which the notification of the error is displayed and confirm details of the error.

In the notification displaying step, the measurement items measured for one sample may be displayed as or in a list on the display unit (33c).

With the configuration explained above, the measurement items displayed in the notification displaying step are measurement items deriving from one sample. Consequently, for example, when measurement results are displayed using the tabs (710), the information obtained by selecting any of the tabs (710) on the measurement result display screen (700) derives from the one sample. Therefore, the operator of the sample analyzer (30) can view the cross-cutting information on the one sample.

The display method may further include an error detecting step of detecting an error of the measurement result of each of the measurement items.

With the configuration explained above, the sample analyzer (30) can detect an error concerning the measurement result and displays the error in association with the measurement item.

The display method may further include a list displaying step of displaying information on the samples as or in a list, and the measurement-result displaying step and the notification displaying step may be executed in response to selection of at least one of the samples.

With the configurations explained above, the measurement result displaying step and the notification displaying step are displayed in response to selection of a specific sample by the operator of the sample analyzer (30) from the samples displayed as or in a list in the list displaying step. That is, the operator of the sample analyzer (30) selects a sample, whereby a notification concerning a measurement result is displayed in association with a measurement item to which the measurement result belongs. Accordingly, the operator of the sample analyzer (30) can quickly recognize the notification concerning the measurement result of the selected sample and which measurement item the notification concerns.

A name of the measurement item associated with the tab (710) may be displayed on the tab (710).

With the configuration explained above, an item name of the measurement item is displayed on each of the tabs (710) on the measurement result display screen (700). Accordingly, the operator of the sample analyzer (30) can easily recognize (i) what is the measurement item and (ii) which measurement item is notified.

In the notification displaying step, the notification or information indicating the notification concerning the measurement result may be displayed in a form which varies or differs among notifications.

With the configuration explained above, the notification concerning the measurement result is displayed in a form which varied depending on the notification on the measurement result display screen (700). Accordingly, the operator of the sample analyzer (30) can easily recognize not only the presence of the notification but also a type of the notification.

In the displaying step, the measurement result of the measurement item specified by the measurement item selected by an operator of the sample analyzer (30) and the notification concerning the measurement result may be displayed on the same screen.

With the configuration explained above, information associated with the selected measurement item and the notification concerning the measurement result are displayed on the same screen on the measurement result display screen (700). Accordingly, even if the operator of the sample analyzer (30) selects a measurement result, a notification concerning which is not displayed, recognition of the notification concerning the measurement result is not prevented.

The tab (710) may be displayed such that the tab (710c), on which the notification concerning the measurement result is displayed, is displayed in predetermined display order.

With the configuration explained above, the tab (710c), on which the notification concerning the measurement result is displayed, is displayed in order decided in advance on the measurement result display screen (700). Consequently, for example, it is possible to adopt a display method of "displaying the tab (710c), on which the notification concerning the measurement result is displayed, at the left end of the tabs (710). Accordingly, labor and time of the operator of the sample analyzer (30) in selecting the tab (710c), on which the notification concerning the measurement result is displayed, are saved. Alternatively, it is also possible to set "the tab (710c), on which the notification concerning the measurement result is displayed", in a selected state from the beginning and display information on the tab (710c), on which the notification concerning the measurement result is displayed".

A sample analyzer (30) according to one or more aspects a sample analyzer (30) including a controller (an analysis controller 33a) and a display unit (33c), the sample analyzer (30) displaying measurement results of measurement items. The controller (the analysis controller 33a) executes: a notification displaying step of selectably displaying each of the measurement items on a display unit (33c) and displaying a notification concerning the measurement result on the display unit (33c) in association with the measurement items; and a measurement-result displaying step of displaying, in response to selection of at least one of the measurement items, a measurement result of the selected measurement item on the display unit (33c).

With the configuration explained above, there is provided the sample analyzer (30) in which, on a display screen for causing an operator of the sample analyzer (30) to select a measurement item in order to display a measurement result, a notification concerning a certain measurement result is displayed on the display unit (33c) in association with the measurement item. The operator of such a sample analyzer (30) can recognize, in a stage for selecting the measurement item, that the notification concerning the measurement result is present.

In order to solve the problems, a computer program according to one or more aspects is a computer program used in a sample analyzer (30) that displays measurement results of measurement items, the computer program causing a computer of the sample analyzer (30) to execute: a notification displaying step of selectably displaying each of the measurement items on a display unit (33c) and displaying a notification concerning the measurement result on the display unit (33c) in association with the measurement items; and a measurement-result displaying step of displaying, in response to selection of at least one of the measurement items, a measurement result of the selected measurement item on the display unit (33c).

With the configuration explained above, there is provided the computer program for causing the sample analyzer (30) to operate such that, on a display screen for causing an operator of the sample analyzer (30) to select a measurement item in order to display a measurement result, a notification concerning a certain measurement result is displayed on the display unit (33c) in association with the measurement item. The operator of such a sample analyzer (30), in which such a computer program is used, can recognize, in a stage for selecting the measurement item, that the notification concerning the measurement result is present.

The computer program is recorded in a computer-readable recording medium according to one or more aspects.

With the configuration explained above, it is possible to cause the computer program to be present while involving a physical entity.

According to one or more aspects, there is provided a method of displaying a measurement result by a sample analyzer with which a notification concerning a measurement result can be easily recognized.

Embodiments are explained below with reference to the drawings.

[Overall Structure of Sample Analyzer]

First, the structure of a sample analyzer 30 according to an embodiment is explained with reference to FIGS. 1 and 2. As illustrated in FIG. 1, the sample analyzer 30 includes a measuring unit 32 and an analyzing unit 33.

Figure 2:
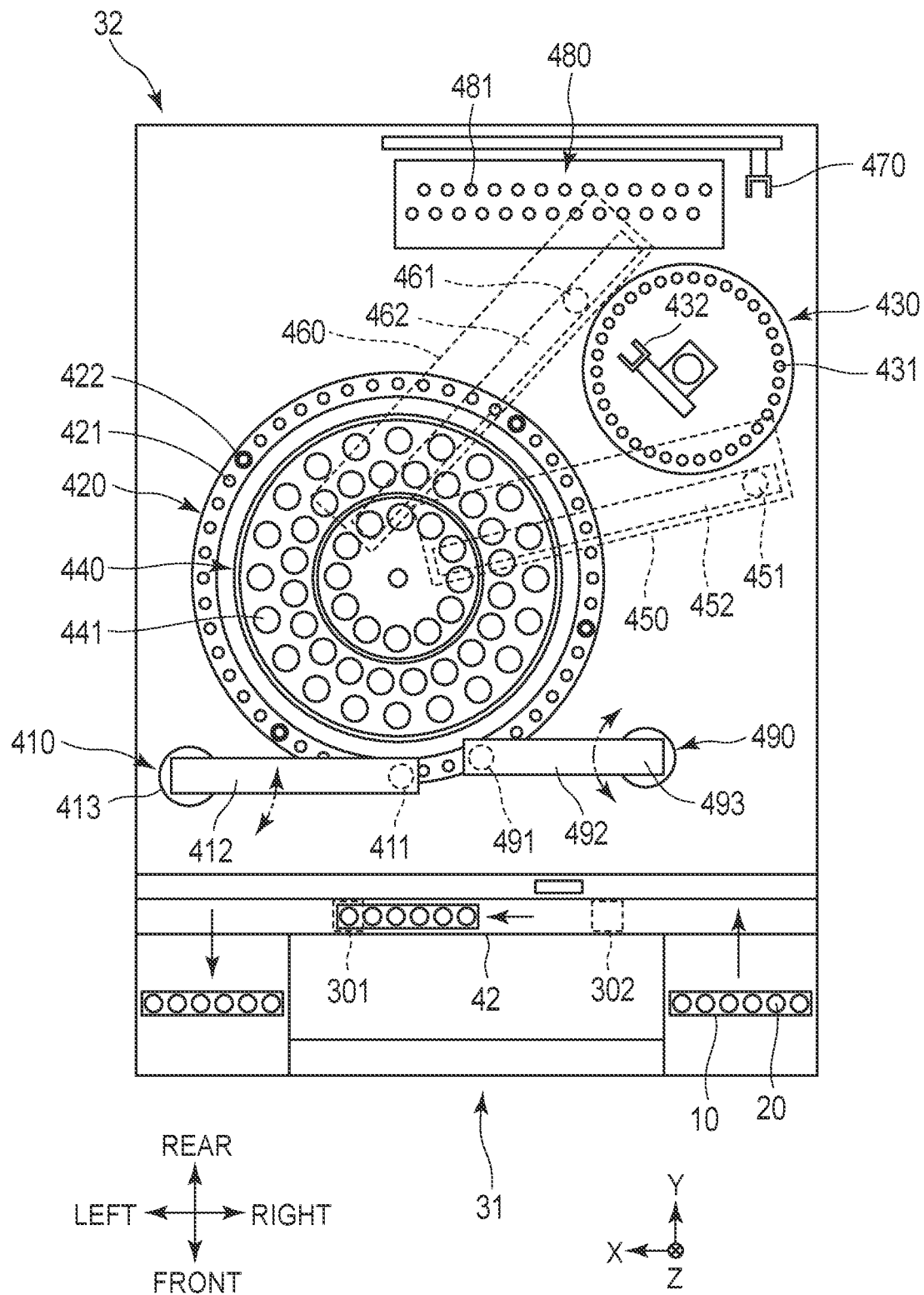
FIG. 2 is a diagram illustrating a top view schematically illustrating a measuring unit of the sample analyzer according to an embodiment.

The measuring unit 32 includes a measurement controller 32a, a measurement memory 32b, and various functional units illustrated in FIG. 2. The measurement controller 32a is, for example, a CPU. The measuring memory 32b is, for example, a ROM, a RAM, or a hard disk. The measurement controller 32a controls the units in the measuring unit 32 according to programs and data stored in the measurement memory 32b. The measurement controller 32a performs, for example, measurement necessary for a blood coagulation analysis of a sample and sends a result of the measurement to the analyzing unit 33.

The analyzing unit 33 includes an analysis controller 33a, an analysis memory 33b, a display unit 33c, and an input unit 33d. The analysis controller 33a is, for example, a CPU. The analysis memory 33b is, for example, a ROM, a RAM, or a hard disk. The analysis controller 33a controls the units in the analyzing unit 33 and the measuring unit 32 according to programs and data stored in the analysis memory 33b. The display unit 33c is, for example, a liquid crystal display. The input unit 33d is, for example, a mouse and a keyboard. The display unit 33c and the input unit 33d may be integrally configured by, for example, a display of a touch panel type.

The analysis controller 33a may be realized by hardware (for example, using a logic circuit formed in an integrated circuit or the like). Alternatively, the analysis controller 33a may be realized by software (for example, using a device including one or more processors and a computer-readable recording medium storing a program for causing a computer to realize functions).

The analysis controller 33a performs, for example, a blood coagulation analysis of a sample based on a measurement result received from the measuring unit 32. In this case, the analysis controller 33a performs an analysis concerning measurement item such as PT, APTT, Fbg, an exogenous coagulation factor, an endogenous coagulation factor, a coagulation XIII-th factor, HpT, TTO, FDP, D dimer, PIC, FM, ATIII, Plg, APL, PC, VWF:Ag, VWF:RCo, ADP, collagen, and epinephrine.

As illustrated in FIG. 2, the measuring unit 32 is arranged behind a transporter 31. The measuring unit 32 performs measurement necessary for the blood coagulation analysis. In this case, a sample stored in a sample container 20 is plasma.

Note that liquid stored in the sample container 20 as the sample is not limited to the plasma. That is, the sample stored in the sample container 20 is not limited to the plasma and may be whole blood, serum, urine, lymph, celomic fluid, or the like. For example, when the measuring unit 32 performs measurement concerning a blood cell test on the sample, the sample can be whole blood. For example, when the measuring unit 32 performs measurement concerning a blood coagulation test, an immune test, or a biochemical test on the sample, the sample can be plasma. For example, when the measuring unit 32 performs measurement concerning the immune test or the biochemical test on the sample, the sample can be serum.

The measuring unit 32 includes a sample dispensing unit 410, a reaction container table 420, a heating table 430, a reagent table 440, reagent dispensing units 450 and 460, a transferring unit 470, a detecting unit 480, and a sample dispensing unit 490.

The sample dispensing unit 410 includes an aspirator 411, an arm 412, and a mechanism unit 413. The sample dispensing unit 410 aspirates, via the aspirator 411, the sample from the sample container 20 set in a sample rack 10 and located in an aspiration position 301. Thereafter, the sample dispensing unit 410 discharges the aspirated sample to a reaction container 422 held by holding holes 421 of the reaction container table 420.

Like the sample dispensing unit 410, the sample dispensing unit 490 includes an aspirator 491, an arm 492, and a mechanism unit 493. The aspirator 491 is set at the distal end of the arm 492. The aspirator 491 is configured by a nozzle. The mechanism unit 493 is configured to rotate the arm 492 in the circumferential direction and move the arm 492 in the up-down direction. Consequently, the aspirator 491 is capable of moving in the circumferential direction and the up-down direction.

The sample dispensing unit 490 is set in the sample rack 10. The sample dispensing unit 490 lowers the aspirator 491 from the upper side with respect to the sample container 20 positioned in an aspiration position 302 on a conveying path 42a of a rack transporter 42 and inserts the aspirator 491 into the sample container 20. The sample dispensing unit 490 aspirates the sample from the sample container 20 via the aspirator 491 and discharges the aspirated sample to the reaction container 422 held in the holding holes 421 of the reaction container table 420.

The reaction container table 420 has a ring shape in a plan view and is arranged on the outer side of the reagent table 440. The reaction container table 420 is configured to be rotatable in the circumferential direction. The reaction container table 420 includes the holding holes 421 for holding the reaction container 422.

The heating table 430 includes holding holes 431 for holding the reaction container 422 and a transferring unit 432 for transferring the reaction container 422. The heating table 430 has a circular contour in a plan view and is configured to be rotatable in the circumferential direction. The heating table 430 heats the reaction container 422 set in the holding holes 431 to 37° C.

When the sample is discharged to the reaction container 422 held by the reaction container table 420, the reaction container table 420 is rotated and the reaction container 422 storing the sample is transferred to the vicinity of the heating table 430. The transferring unit 432 of the heating table 430 grips the reaction container 422 and sets the reaction container 422 in the holding holes 431 of the heating table 430.

The reagent table 440 is configured such that reagent containers 441 storing reagents used for measurement necessary for the blood coagulation analysis can be set on the reagent table 440. The reagent table 440 is configured to be rotatable in the circumferential direction. The reagent containers 441 storing reagents used in measurement of measurement items are set on the reagent table 440.

The reagent dispensing unit 450 includes a nozzle 451 and a mechanism unit 452. The mechanism unit 452 is configured to move the nozzle 451 in the horizontal direction to traverse the reagent table 440 and move the nozzle 451 in the up-down direction. Similarly, the reagent dispensing unit 460 includes a nozzle 461 and a mechanism unit 462. The mechanism unit 462 is configured to move the nozzle 461 in the horizontal direction to traverse the reagent table 440 and move the nozzle 461 in the up-down direction. The reagent dispensing units 450 and 460 are set on the lower side of a housing upper surface of the measuring unit 32.

The reagent dispensing units 450 and 460 dispense the reagent into the reaction container 422 heated by the heating table 430. In the dispensing of the reagent, the transferring unit 432 or the transferring unit 470 takes out the reaction container 422 from the holding holes 431 of the heating table 430 and positions the reaction container 422 in a predetermined position near the heating table 430. The reagent dispensing units 450 and 460 aspirate the reagent from the reagent containers 442 via the nozzles 451 and 461 and discharge the aspirated reagent to the reaction container 422. Consequently, the reagent is mixed in the sample and a measurement specimen is prepared. Thereafter, the transferring unit 470 sets the reaction container 422 in holding holes 481 of the detecting unit 480.

A measurement principle of the detecting unit 480 is, for example, a coagulation method, a synthetic substrate method, immunonephelometry, or an agglutination method. The detecting unit 480 includes holding holes 481. The detecting unit 480 irradiates light on the reaction container 422 set in the holding holes 481, receives the light transmitted through a measurement specimen, and outputs a signal corresponding to light reception intensity. The measurement controller 32a of the measuring unit 32 stores, as a measurement result, a signal output from the detecting unit 480 and transmits the measurement result to the analyzing unit 33.

[Display Mechanism of the Measurement Result Display Screen]

Figure 3A:
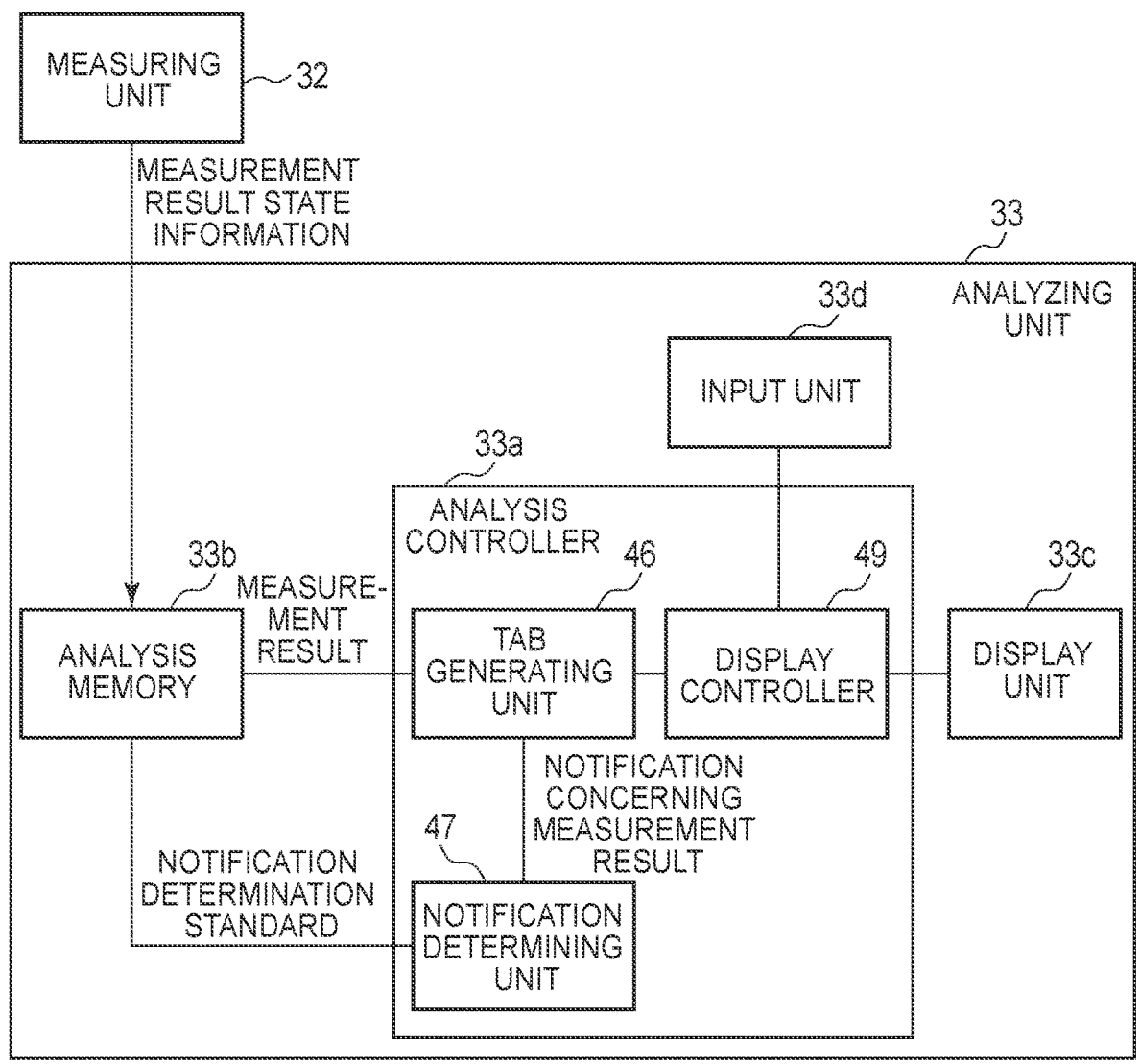
FIG. 3A is a block diagram illustrating units related to display of a measurement result display screen in the sample analyzer according to an embodiment.
Figure 3B:
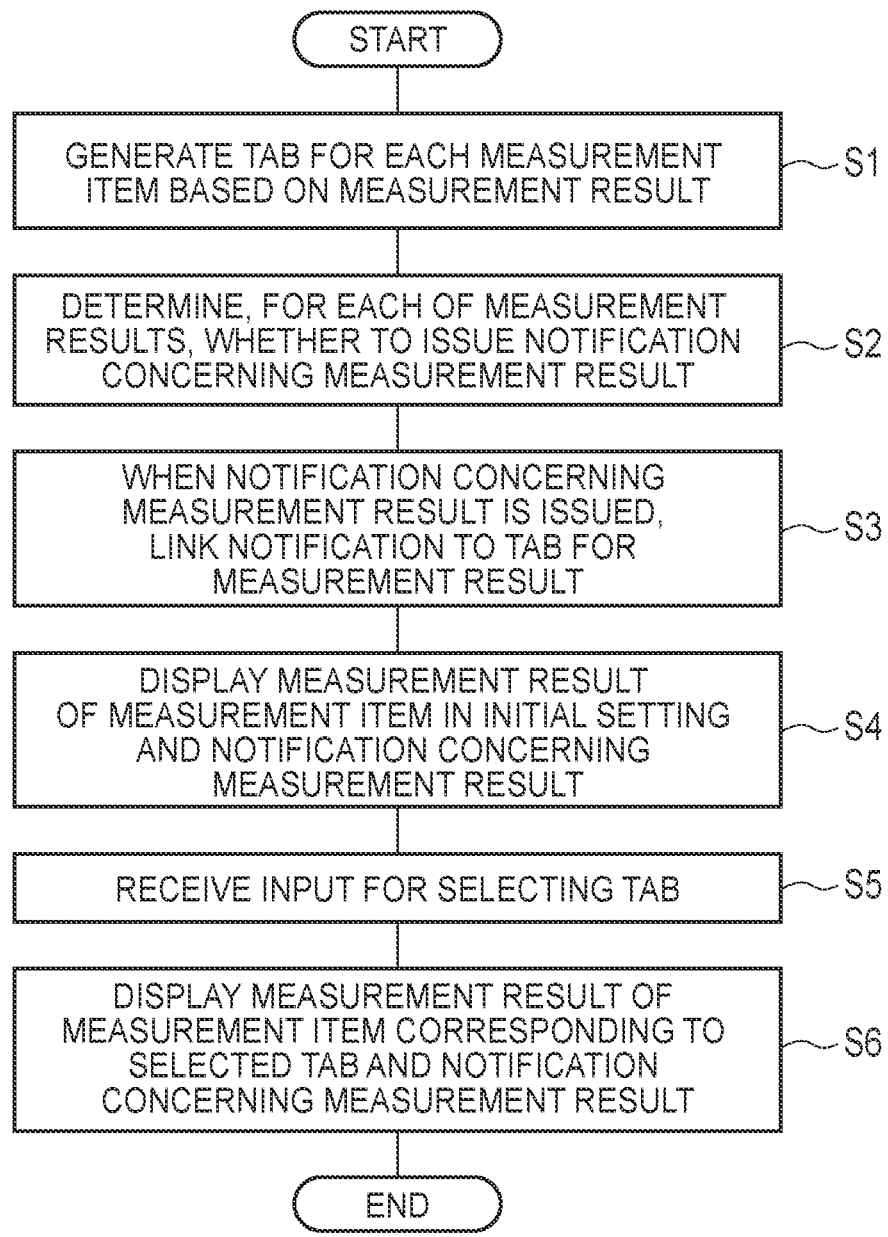
FIG. 3B is a flow diagram illustrating a sequence of processing at the time when the measurement result display screen is displayed in the sample detector according to an embodiment.

A mechanism in displaying a measurement result display screen 700 on the display unit 33c is explained with reference to FIGS. 3A and 3B. FIG. 3A is a block diagram illustrating units related to the display of the measurement result display screen 700.

For example, a measurement result acquired by the measuring unit 32 is stored in the analysis memory 33b.

A tab generating unit 46 reads out a measurement result from the analysis memory 33b, generates the tab 710 for each of measurement items, and sends the tab 710 to the display controller 49. When a notification determining unit 47 determines that "a notification is issued" concerning a certain measurement result, the tab generating unit 46 links the notification to a tab for the measurement result and sends the notification to the display controller 49.

The notification determining unit 47 reads out measurement results from the analysis memory 33b. Thereafter, the notification determining unit 47 compares each of the measurement results with a notification determination standard and determines presence or absence of a notification concerning the measurement result. When determining that "a notification concerning the measurement result is present", the notification determining unit 47 sends the notification concerning measurement result to the tab generating unit 46. The notification determination standard refers to a standard for determining presence of absence of the notification concerning the measurement result. In an example, the standard is a standard concerning a normal value of the measurement result.

The input unit 33d receives an operation input of the operator to the analyzing unit 33. A result of the operation input by the operator is sent from the input unit 33d to the display controller 49. Finally, a display screen in the display unit 33c changes.

The display controller 49 generates a display screen based on information received from the tab generating unit 46 and the input unit 33d and causes the display unit 33c to display the display screen.

Among the functional blocks explained above, the tab generating unit 46, the notification determining unit 47, and the display controller 49 may be implemented by, for example, a CPU.

A sequence of processing at the time when the measurement result display screen 700 is displayed is explained with reference to FIG. 3B.

In S1, the tab generating unit generates a tab, or a graphical control element, for each of the measurement items based on a measurement result. Specifically, the tab generating unit 46 reads out a measurement result from the analysis memory 33b and generates the tab 710 for each of the measurement items.

In S2, the notification determining unit 47 determines, for each of the measurement items, whether or not to issue a notification concerning the measurement result. More specifically, the notification determining unit 47 reads out a measurement result of each of the measurement items and the notification determination standard from the analysis memory 33b and compares the measurement result and the notification determination standard to thereby determine whether or to issue a notification concerning the measurement result. For a measurement item determined as "a notification is issued", the notification concerning the measurement result is sent to the tab generating unit 46.

In S3, the tab generating unit 46 links the notification concerning the measurement result to a tab 710c of the measurement item determined as "a notification is issued".

In S4, the display controller 49 causes the display unit 33c to display (i) a measurement result of the measurement item in initial setting and (ii) a notification concerning the measurement result. That is, both of the notification displaying step and the display of the measurement result of the measurement item in the initial setting are performed. The measurement item in the initial setting can be, for example, a measurement item displayed on the tab 710 at the leftmost end.

In S5, the input unit 33d receives an input for selecting the tab 710 by the operator of the sample analyzer 30.

In S6, the display controller 49 causes the display unit 33c to display (i) a measurement result of a measurement item associated with the tab selected in S5 and (ii) a notification concerning the measurement result. That is, both of the measurement result displaying step and the notification displaying step are performed.

[Screen Configuration]

A screen configuration of the sample analyzer 30 is explained with reference to FIG. 4 to FIG. 11D.

[Job List Display Screen]

Figure 4:
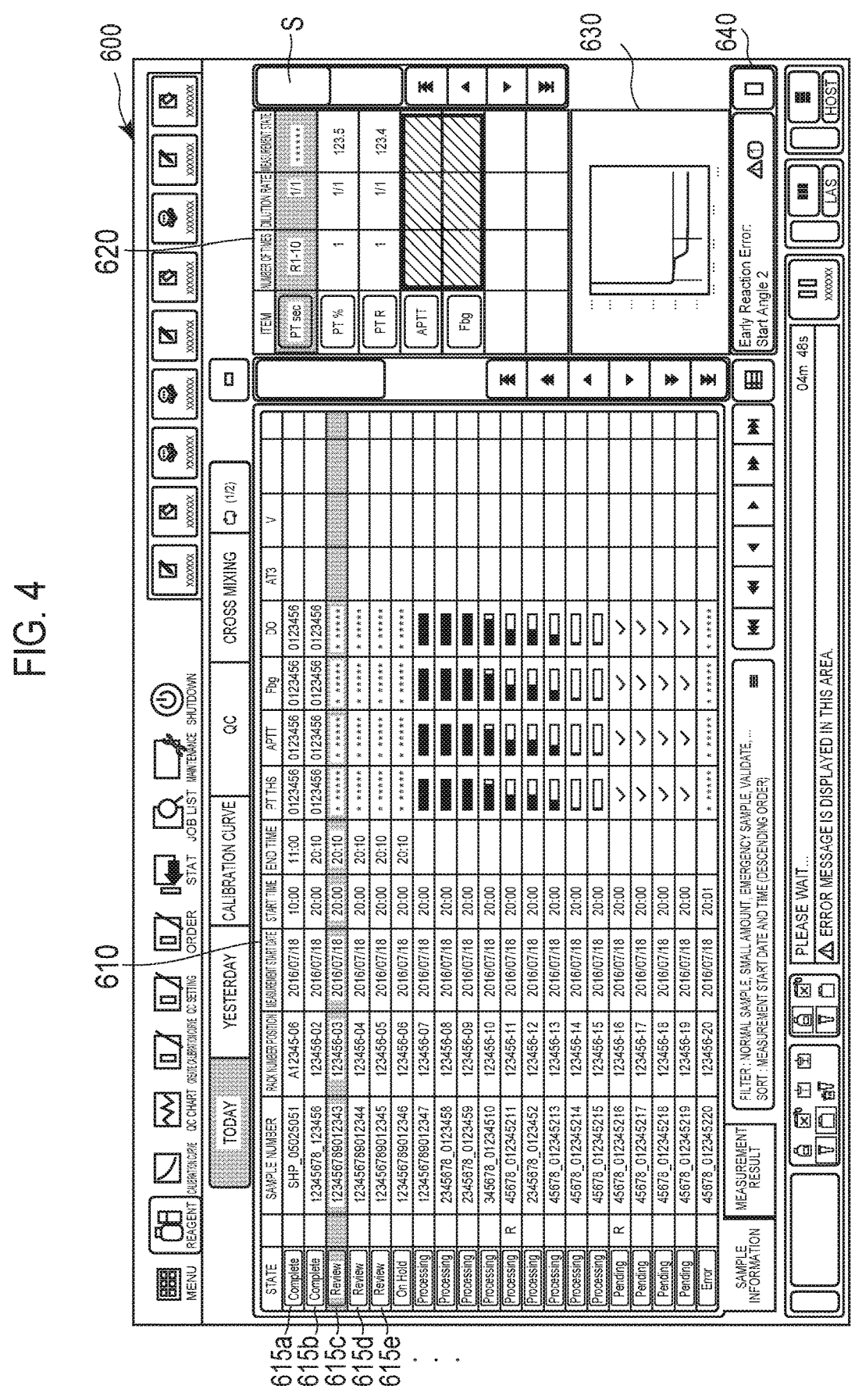

FIG. 4 is a diagram illustrating a screen configuration example of a job list display screen 600 displayed on the display unit 33c of the sample analyzer 30. The job list display screen 600 includes a sample list display region 610, a measurement result display region 620, a reaction curve display region 630, and an error information display region 640.

The sample list display region 610 is a region where a list of samples to be processed by the sample analyzer 30 is displayed. Information on one sample is displayed in each one row in the sample list display region 610. That is, each of rows 615a, 615b, 615c, 615d, 615e, and the like represents information on one sample. Any one of these rows is selected (in FIG. 4, the row 615c is selected), whereby information on a sample specified in the row is displayed in the measurement result display region 620, the reaction curve display region 630, and the error information display region 640. When a predetermined operation (double touch or the like) is performed in a state where a certain row is selected, a screen transitions to the measurement result display screen 700 of a sample specified in the row (see FIG. 5).

In the sample list display region 610, a row of "state" indicates in what kind of a state the sample is. In the example illustrated in FIG. 4, "complete" indicates that "measurement is completed", "Review" indicates that "an error is present in a measurement result", "On Hold" indicates that "although measurement is completed, since a calibration curve for which validation is performed is absent, there is a measurement item for which parameters are not calculated", "Processing" indicates that "measurement is in progress", "Pending" indicates "before measurement", and "Error" indicates that "measurement fails".

A measurement result of a sample specified in a row selected in the sample list display region 610 is displayed in the measurement result display region 620. When parameters are calculated for one measurement item, a measurement result is displayed for each of the parameters. In the example illustrated in FIG. 4, three kinds of parameters "PT sec (a prothrombin time represented in second unit)", "PT% (prothrombin activity)", and "PT R (a prothrombin ratio)" are displayed from a test item "PT (a prothrombin time)". Further, results of test items "APTT (an activated partial thromboplastin time)" and "Fbg (a fibrinogen amount)" are also displayed. Note that, in a "measurement state" column of the measurement result display region 620, a part indicated by asterisks "******" is a part where an error occurs. In the example illustrated in FIG. 4, a measurement result of PT sec is a part where an error occurs.

A reaction curve of a measurement item specified in the row selected in the measurement result display region 620 is displayed in the reaction curve display region 630. In the example illustrated in FIG. 4, PT sec is selected in the measurement result display region 620. Since PT sec is a parameter of the measurement item PT, a reaction curve of PT is displayed.

An error information on a parameter specified in the row selected in the measurement result display region 620 is displayed in the error information display region 640. In the example illustrated in FIG. 4, it is indicated that Start Angle 2 among Early Reaction Errors is seen at PT sec.

In this way, on the job list display screen 600 illustrated in FIG. 4, the operator can confirm the error information by referring to the error information display region 640. However, in the case of the screen configuration illustrated in FIG. 4, the error information displayed in the error information display region 640 is only error information on the parameter selected in the measurement result display region 620. Accordingly, when the numbers of measurement items and parameters increase, rows to be displayed increase. Therefore, it is sometimes necessary to operate the scroll region S in finding where error information is present. Accordingly, a time is sometimes required for recognition of the error information. In the screen configuration illustrated in FIG. 4, one parameter is displayed in one row in the measurement result display region 620. Accordingly, the number of rows tends to increase more than when one measurement item is displayed in one row. Therefore, a time tends to be required for the recognition of the error information.

On the other hand, a screen configuration of a measurement result display screen 700 explained in embodiments below is designed to improve recognizability of error information. Accordingly, the operator can immediately recognize the error information.

[First Embodiment]

Figure 5:
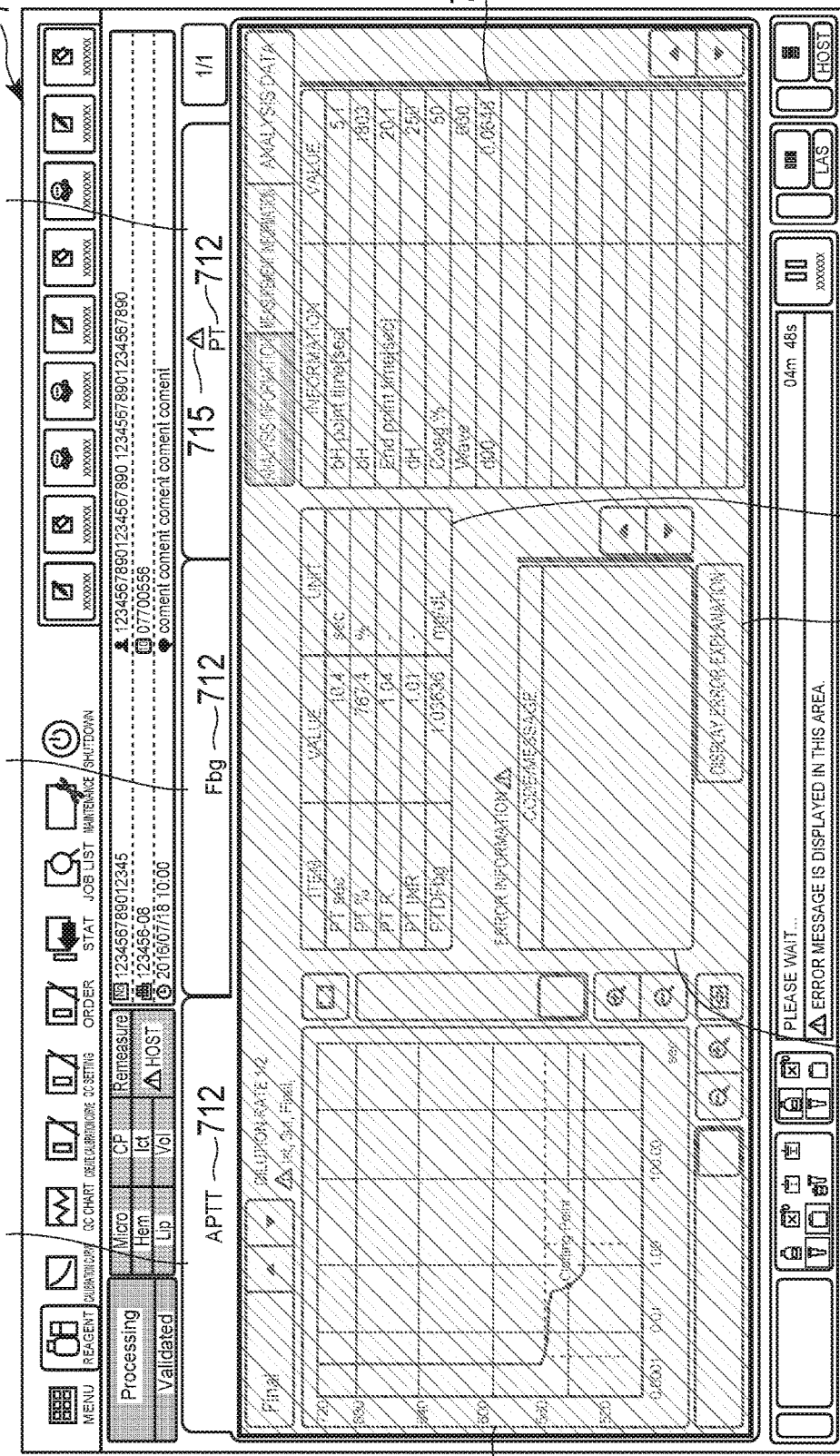
FIG. 5 is a diagram illustrating a measurement result display screen in a first embodiment.

FIG. 5 is a diagram illustrating a screen configuration example of the measurement result display screen 700 in a first embodiment. The measurement result display screen 700 can be transitioned or switched from the job list display screen 600. The measurement result display screen 700 includes a tab 710, a reaction curve display region 720, a measurement result display region 730, a detailed information display region 740, an error information display region 750, and an error explanation display button 760. A reaction curve of a selected measurement item is displayed in the reaction curve display region 720. Detailed information of the selected item is displayed in the detailed information display region. Information on an error that occurs for the selected measurement item is displayed in the error information display region 750. Explanation concerning the error is displayed when the error explanation display button 760 is touched. At this time, an error in which diffraction is displayed is the error selected in the error information display region 750.

The tab 710 is generated for each of measurement items. A measurement-item display section 712 is provided in the tab 710. In a first embodiment, three tabs 710a, 710b, and 710c are generated. The three tabs 710a, 710b, and 710c are respectively associated with measurement items of APTT, Fbg, and PT. When any one of the tabs 710 is selected, information for the selected tab is displayed. That is, the reaction curve display region 720, the measurement result display region 730, the detailed information display region 740, and the error information display region 750 of the measurement item displayed on the measurement-item display section 712 of the selected tab are displayed. FIG. 5 illustrates the measurement result display screen 700 to which the screen has just transitioned from the job list display screen 600. In this initial state, the tab 710a is selected and information on APTT is displayed.

An error notification mark 715 indicating that an error has occurred is displayed on the tab 710c. The tab 710 is always displayed on the measurement result display screen 700 irrespective of which tab is selected. Therefore, the error notification mark 715 is always displayed on the measurement result display screen 700. As a result, by referring to the measurement result display screen 700, the operator can immediately learn in which measurement item an error occurs.

Figure 6:
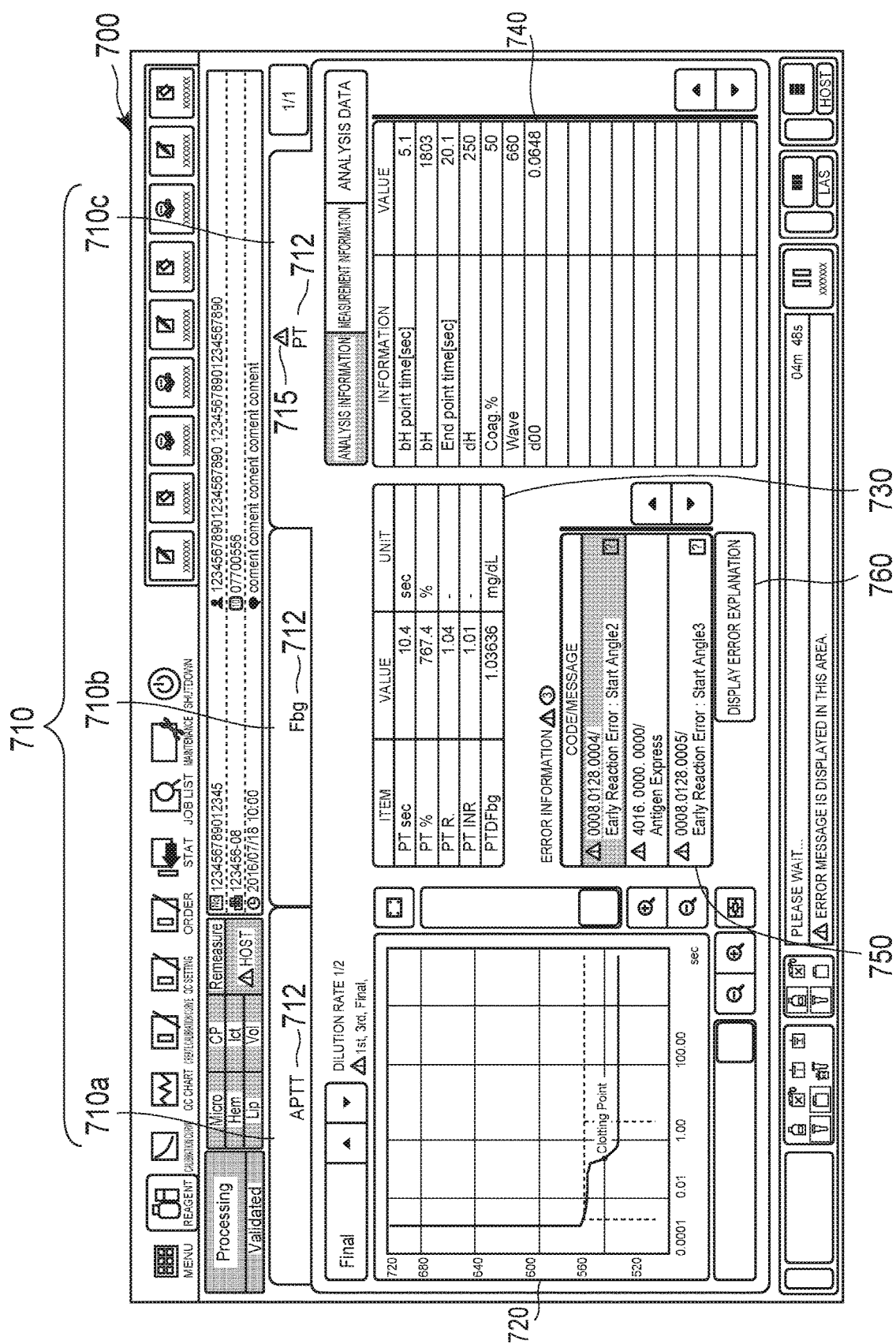
FIG. 6 is a diagram illustrating a screen displayed when a tab, on which an error notification mark is displayed, is selected from the screen illustrated in FIG. 5.

FIG. 6 is a diagram illustrating a state where the tab 710c is selected on the measurement result display screen 700 illustrated in FIG. 5. In this state, information on PT is displayed. Therefore, by referring to the error information display region 750, the operator can learn what kind of an error occurs. In an example illustrated in FIG. 6, occurrence of Start Angle 2 and Start angle 3, which are early reaction errors, and Antigen Express is displayed.

[Reference Example]

Figure 7:
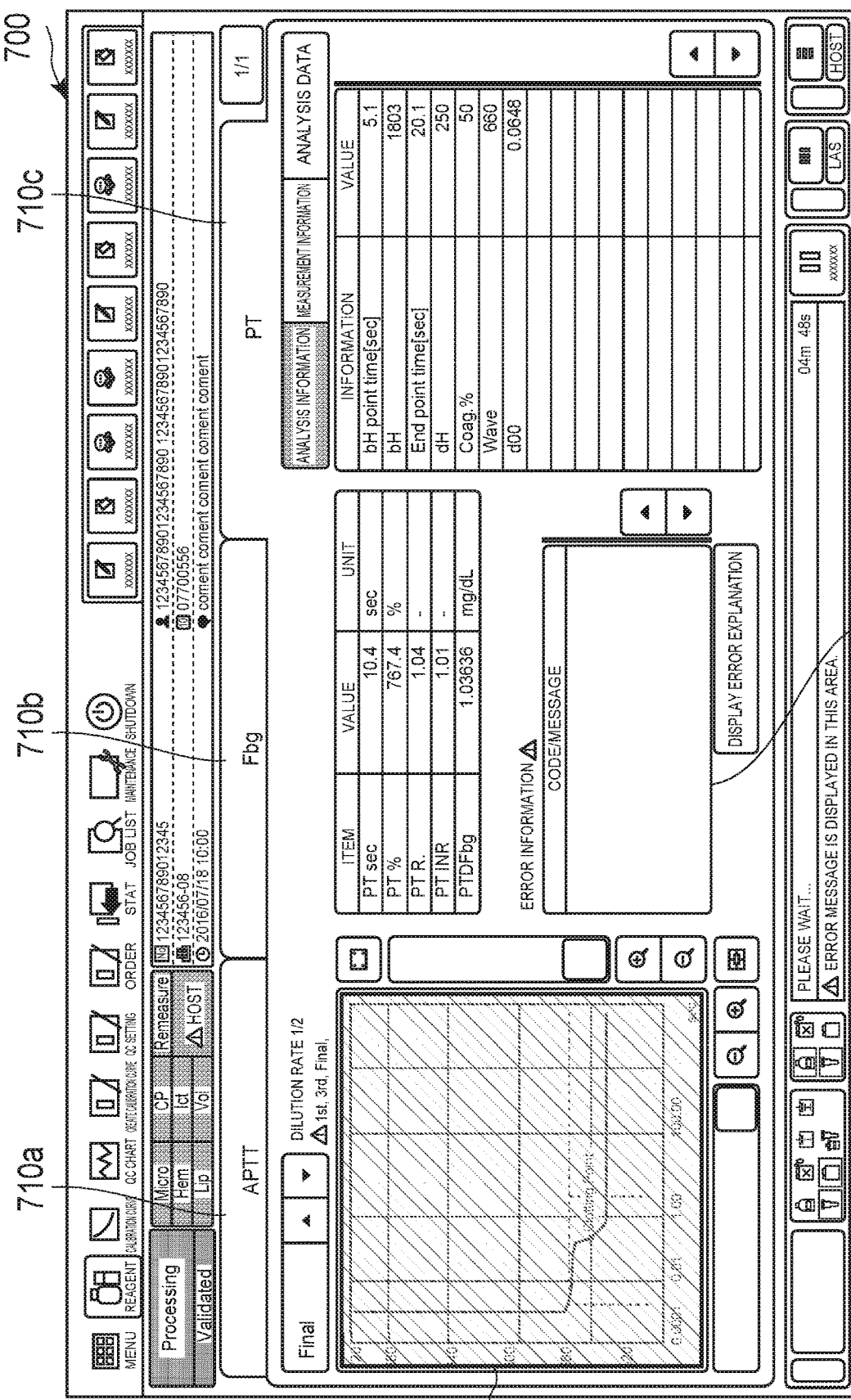
FIG. 7 is a diagram illustrating a measurement result display screen in a reference example.

As a reference example, a diagram illustrating a state where the tab 710c is selected when an error does not occur is illustrated in FIG. 7. In FIG. 7, the error notification mark 715 is not displayed. Information on an error is not displayed in the error information display region 750 either. A reaction curve displayed in the reaction curve display region 720 is a normal reaction curve.

[Second Embodiment]

In a second embodiment, a display method of displaying, in display order decided in advance, tabs indicating that an error occurs is explained.

Figure 8A:
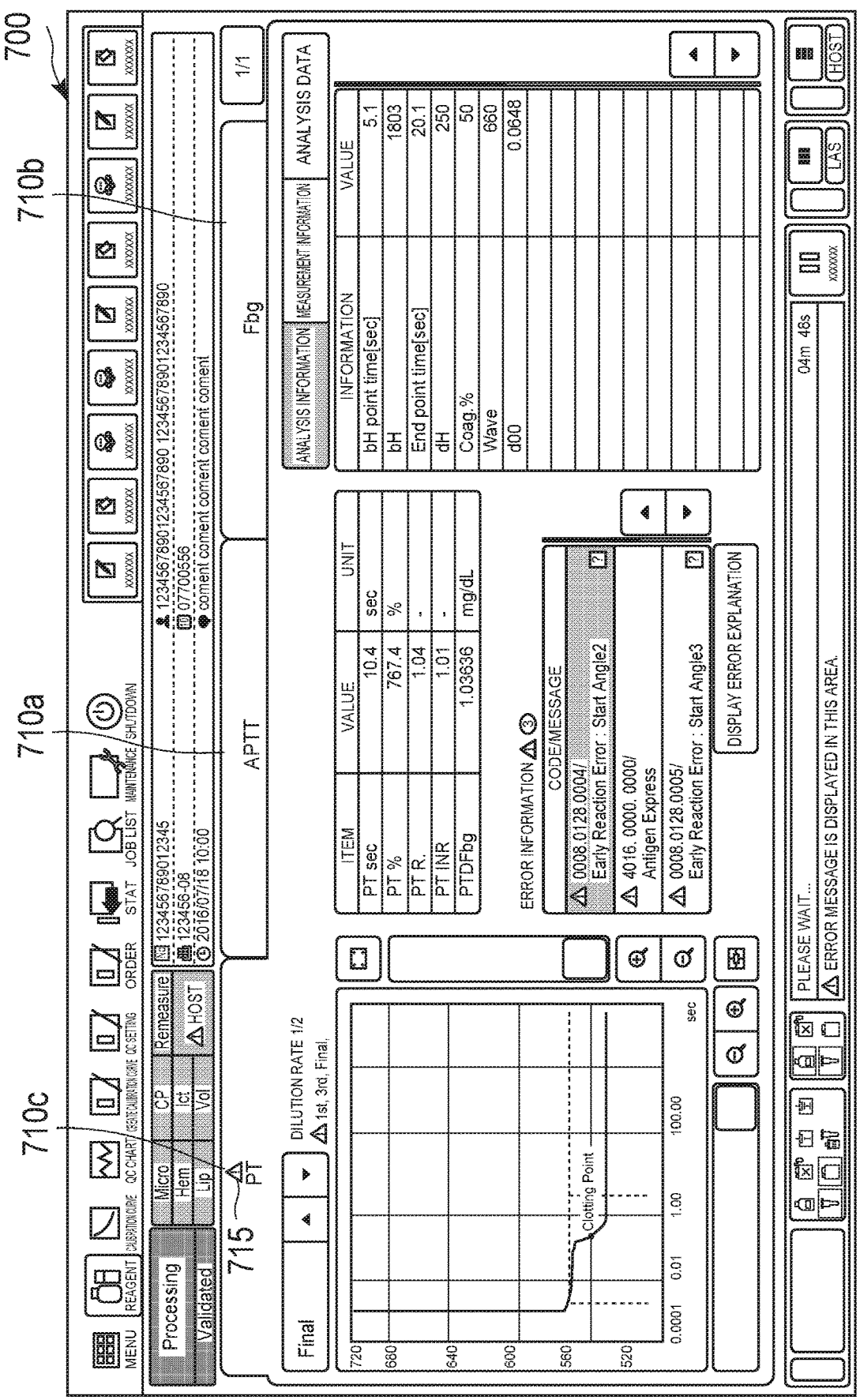
Figure 8B:
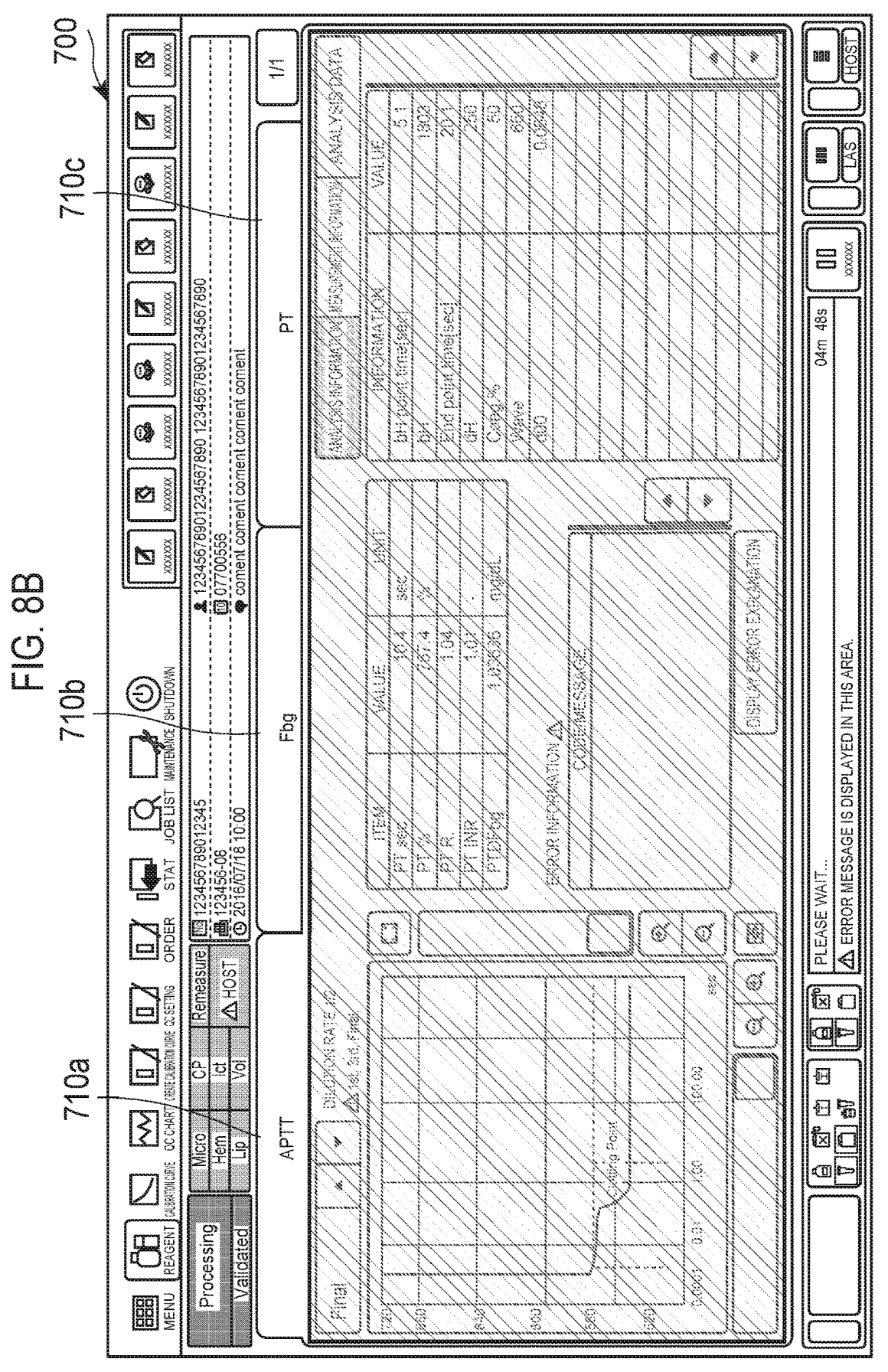

FIG. 8A and FIG. 8B are diagrams each illustrating the measurement result display screen 700 in a second embodiment. In FIG. 8A, the error notification mark 715 is displayed on the tab 710c. Therefore, a display position of the tab 710c is the left end. Since the tabs 710a to 710c are arranged in this way, information on the tab 710c (a measurement result of PT) is displayed first when the screen transitions from the job list display screen 600 to the measurement result display screen 700.

On the other hand, in FIG. 8B, the error notification mark 715 is not displayed in the tab 710c. Therefore, the tabs are still arranged in the order of 710a, 710b, and 710c from the left end in the same manner as usual. When the screen transitions from the job list display screen 600 to the measurement result display screen 700, information on the tab 710a (a measurement result of APTT) is displayed first.

The arrangement of the tabs is changed according to presence or absence of the error notification mark 715 in this way. Consequently, an operator less easily overlooks a tab indicating that an error occurs. If a tab displayed first when the screen transitions from the job list display screen 600 to the measurement result display screen 700 is a tab on which the error notification mark 715 is displayed, it is possible to more effectively notify the occurrence of the error to the operator.

[Third Embodiment]

In a third embodiment, a display method of displaying the error explanation display region 780 is explained.

Figure 9A:
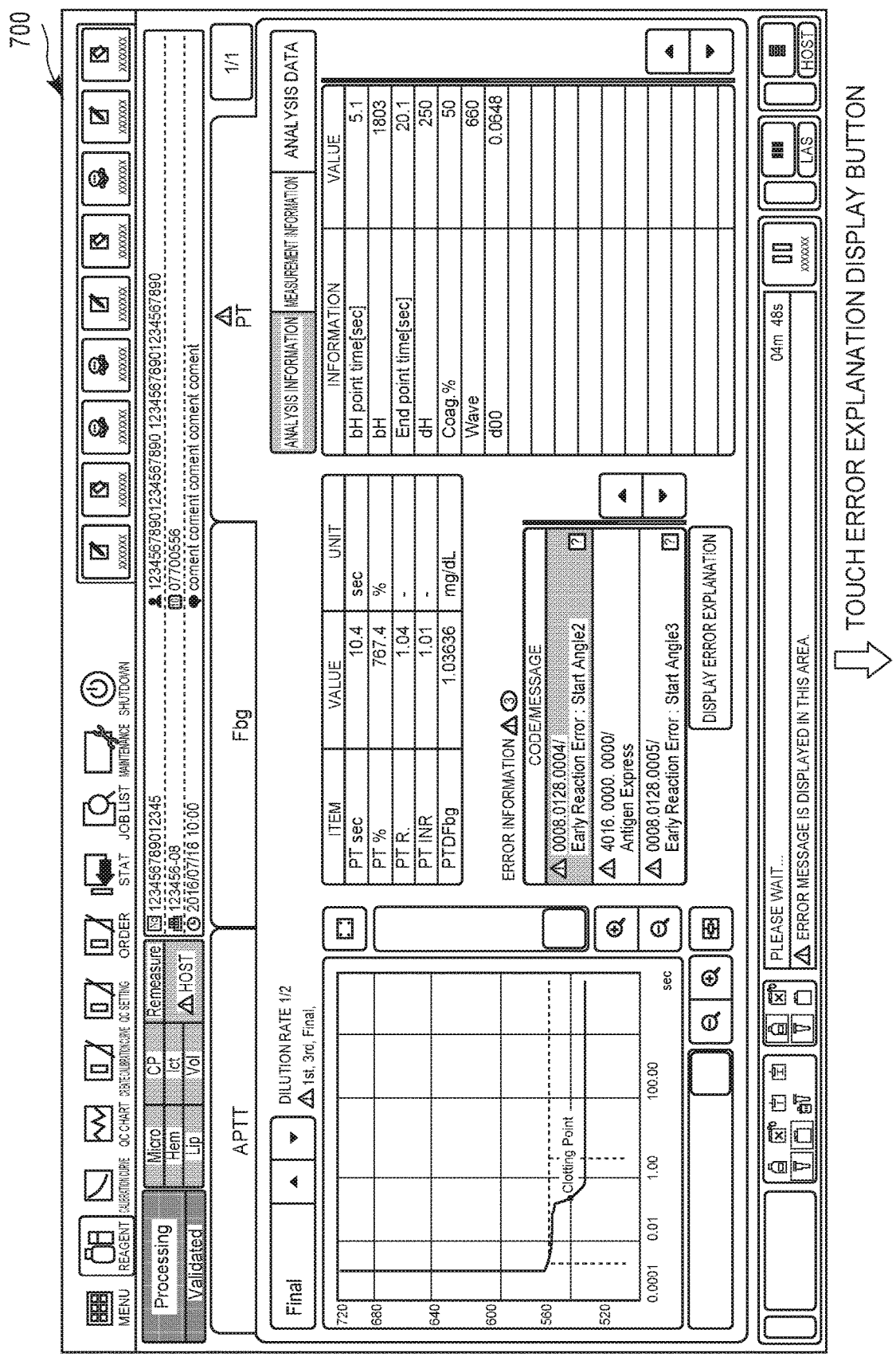
FIG. 9A and FIG. 9B are transition diagrams each illustrating a measurement result display screen in a third embodiment.

FIG. 9A is the same figure as FIG. 6. That is, FIG. 9A is a state where information on the tab 710c on which the error notification mark 715 is displayed (a measurement result of PT) is displayed.

Figure 9B:
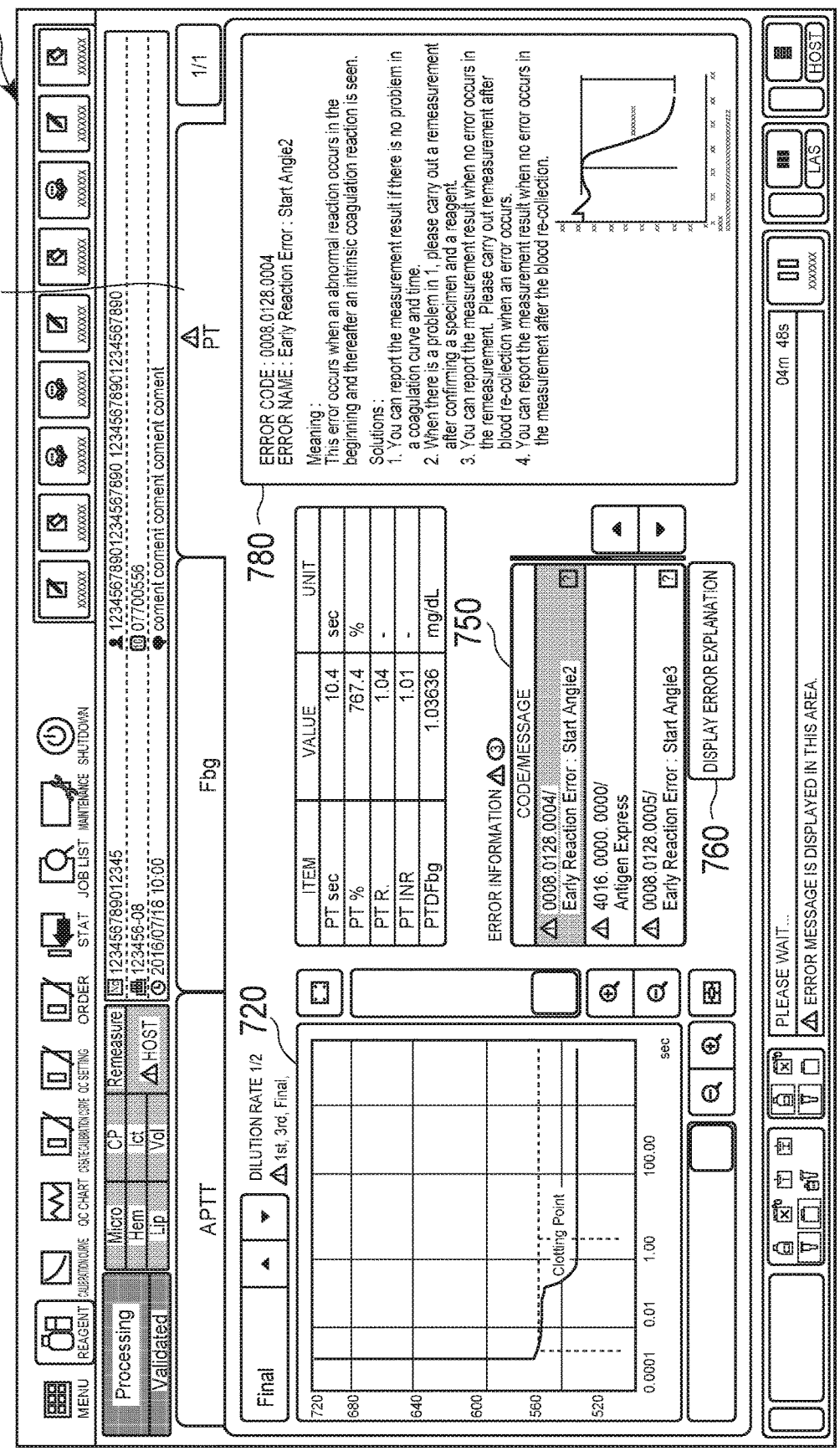

A screen appearing after, from a state of FIG. 9A, one kind of error information is selected from the error information display region 750 (Start Angle 2 is selected in an example illustrated in FIG. 9A and FIG. 9B) and the error explanation display button 760 is touched is FIG. 9B. In this screen, the error explanation display region 780 is displayed and explanation concerning an error selected in the error information display region 750 is displayed (for example, a cause of the error and a solution method for the error).

In a third embodiment, the error explanation display region 780 is displayed on the same screen as a screen on which information on the tab 710c (a measurement result of PT) is displayed. Therefore, an operator can refer to information on the measurement result and the explanation concerning the error at a time. In the example illustrated in FIG. 9A and FIG. 9B, the operator can refer to a reaction curve and various parameters and the explanation concerning the error at a time.

In the past, when referring to such explanation concerning the error, the operator needs to consult a manual based on an error code displayed on the screen. Even if the explanation concerning the error is displayed on the display unit 33c, if the error explanation display region 780 is displayed on a screen separate from the screen on which the information on the tab 710 is displayed or the error explanation display region 780 is displayed as popup, the operator cannot refer to the explanation concerning the error and the information on the measurement result at a time.

According to a third embodiment, labor and time of the operator can be saved by displaying the error explanation display region 780 on the same screen as the screen on which the information on the tab 710c is displayed.

[Modification 1]

In embodiments explained above, when the number of tabs 710 is large, the tabs 710 may be displayed for each of several groups.

Figure 10A:
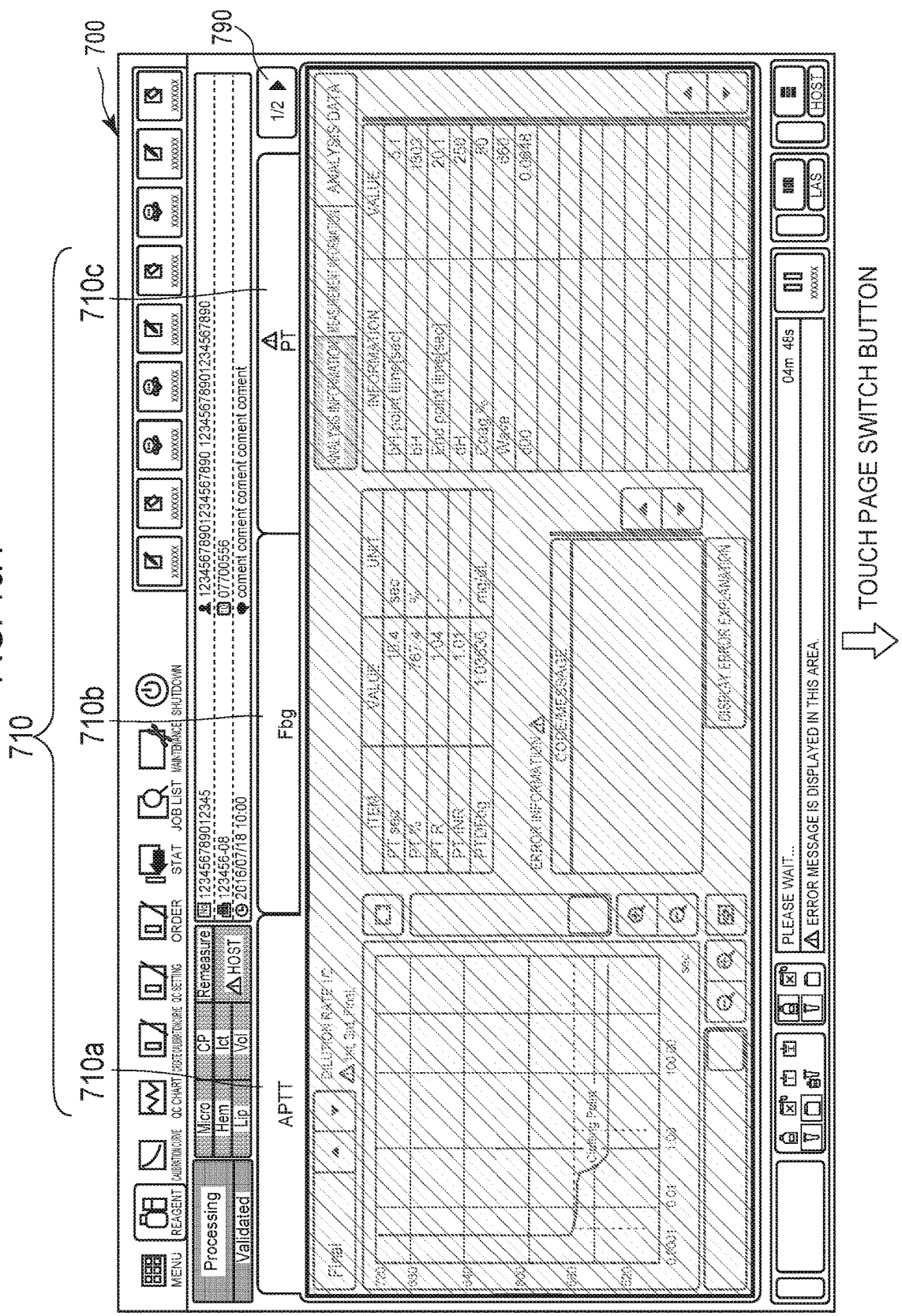
FIG. 10A and FIG. 10B are transition diagrams each illustrating a measurement result display screen in a modification.
Figure 10B:
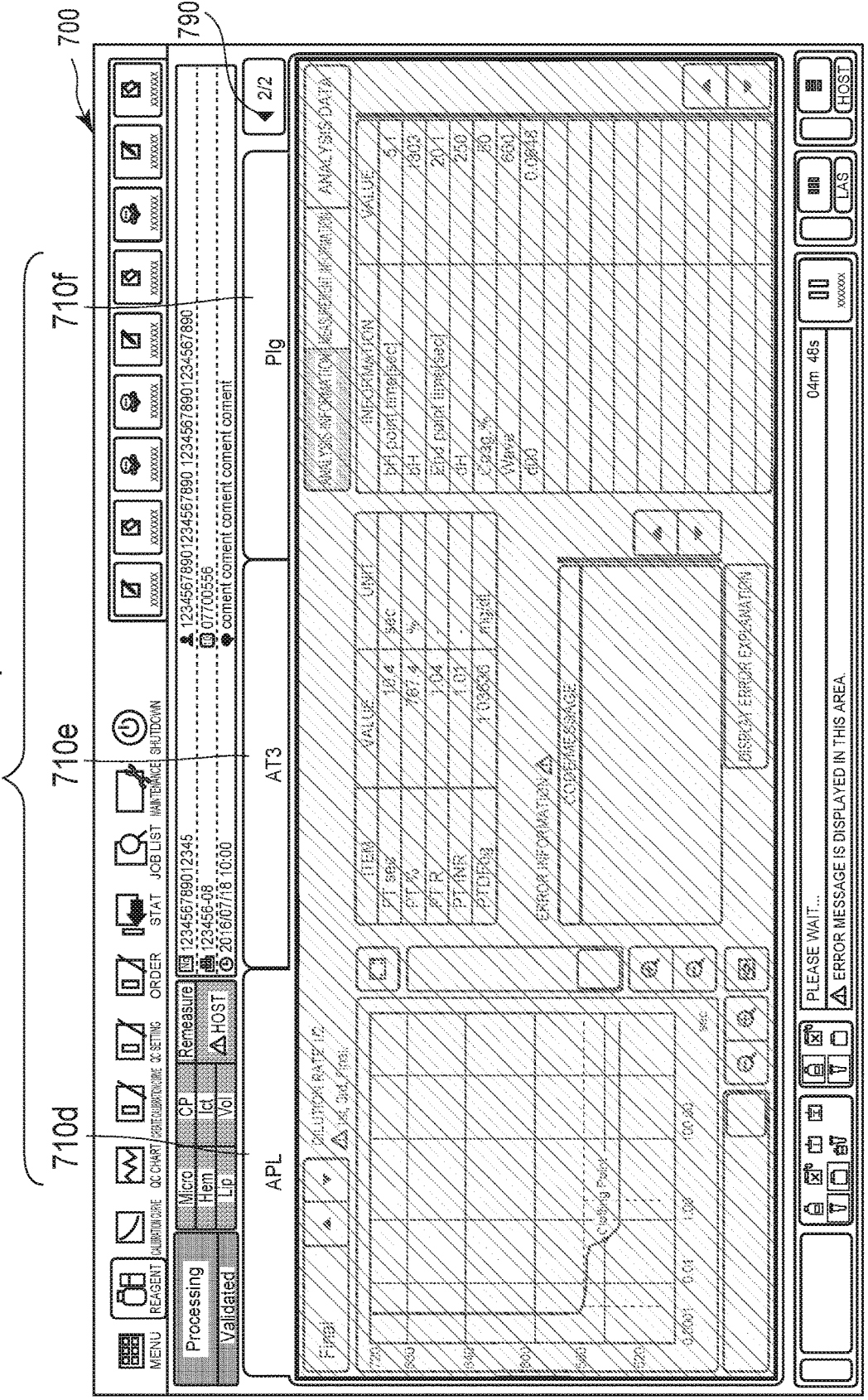

FIG. 10A and FIG. 10B are diagrams illustrating the measurement result display screen 700 in the case in which there are measurement items associated with six tabs 710a to 710f. FIG. 10A is a screen at the time when the measurement result display screen 700 is displayed for the first time. Three tabs 710a, 710b, and 710c are displayed. When a page switch button 790 is touched in a state in FIG. 10A, the screen transitions to a screen in FIG. 10B. Three tabs 710d, 710e, and 710f are displayed on the screen in FIG. 10B.

By limiting the number of tabs appearing in one screen in this way, it is possible to prevent an information amount displayed on the tabs 710 at a time from becoming excessive. Therefore, the operator can easily recognize the measurement items.

Note that, as in this modification, in a configuration in which the tab 710 to be displayed can be switched, it is desirable to include, in a screen at the time when the measurement result display screen 700 is displayed for the first time, tabs concerning frequently used measurement items. For example, when APTT, Fbg, and PT are more frequently used than APL, AT3, and Plg, the tabs 710 are desirably arranged as illustrated in FIG. 10A and FIG. 10B.

[Modification 2]

In the embodiments and the modification explained above, a form in which the measurement result is displayed by the tab is explained. However, the display method according to an embodiment is not limited to the display method using the tab.

For example, measurement items by the sample analyzer 30 may be selected by checkboxes. Specifically, checkboxes for the measurement items are arranged on the measurement result display screen 700. The operator of the sample analyzer 30 selects at least one checkbox. The display screen transitions according to this operation such that a measurement result of a measurement item associated with the selected checkbox is displayed. At this time, the checkboxes may be displayed on the same screen as a screen on which the measurement result is displayed or may not be displayed.

In the example in which the checkboxes are used, a notification concerning the measurement result is displayed by using the checkbox for the measurement item. For example, it is possible to display the notification by changing a font or a color of characters associated with the checkbox, displaying an appropriate mark around the checkbox, or changing a color of the checkbox or the periphery of the checkbox.

In this way, the display method according to an embodiment can be applied to screen design in general for displaying measurement items as or in a list and selecting a specific measurement item to thereby display a measurement result of the measurement item.

[Assumed Scenario]

An example of an assumed scenario in which the display method according to an embodiment can be usefully used is explained with reference to FIG. 11A to FIG. 11 D.

In FIG. 11A, the operator views the job list display screen 600 and learns that a state of a sample specified in the row 615c is "Review". The sample, the state of which is "Review", indicates that an error occurs in a result of measurement. Accordingly, the operator displays the measurement result display screen 700 of the sample specified in the row 615c in order to learn what kind of an error occurs in which measurement item.

Figure 11B:
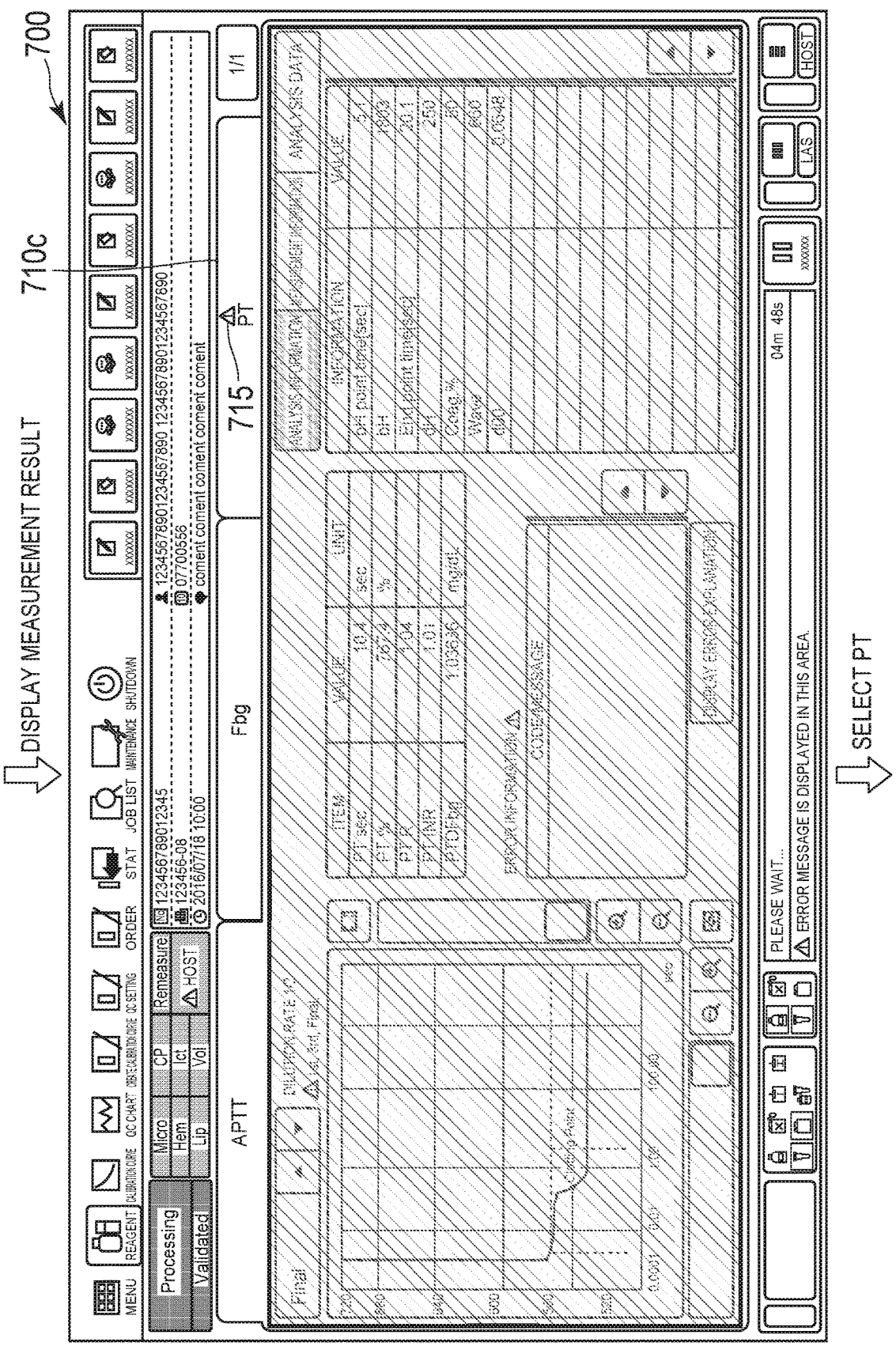

In FIG. 11B, when the measurement result display screen 700 is displayed, the operator immediately recognizes that the error notification mark 715 is displayed on the tab 710c. That is, at this point in time, it is found that an error occurs in a measurement result of PT. Therefore, the operator selects the tab 710c and displays the measurement result of PT.

Figure 11C:
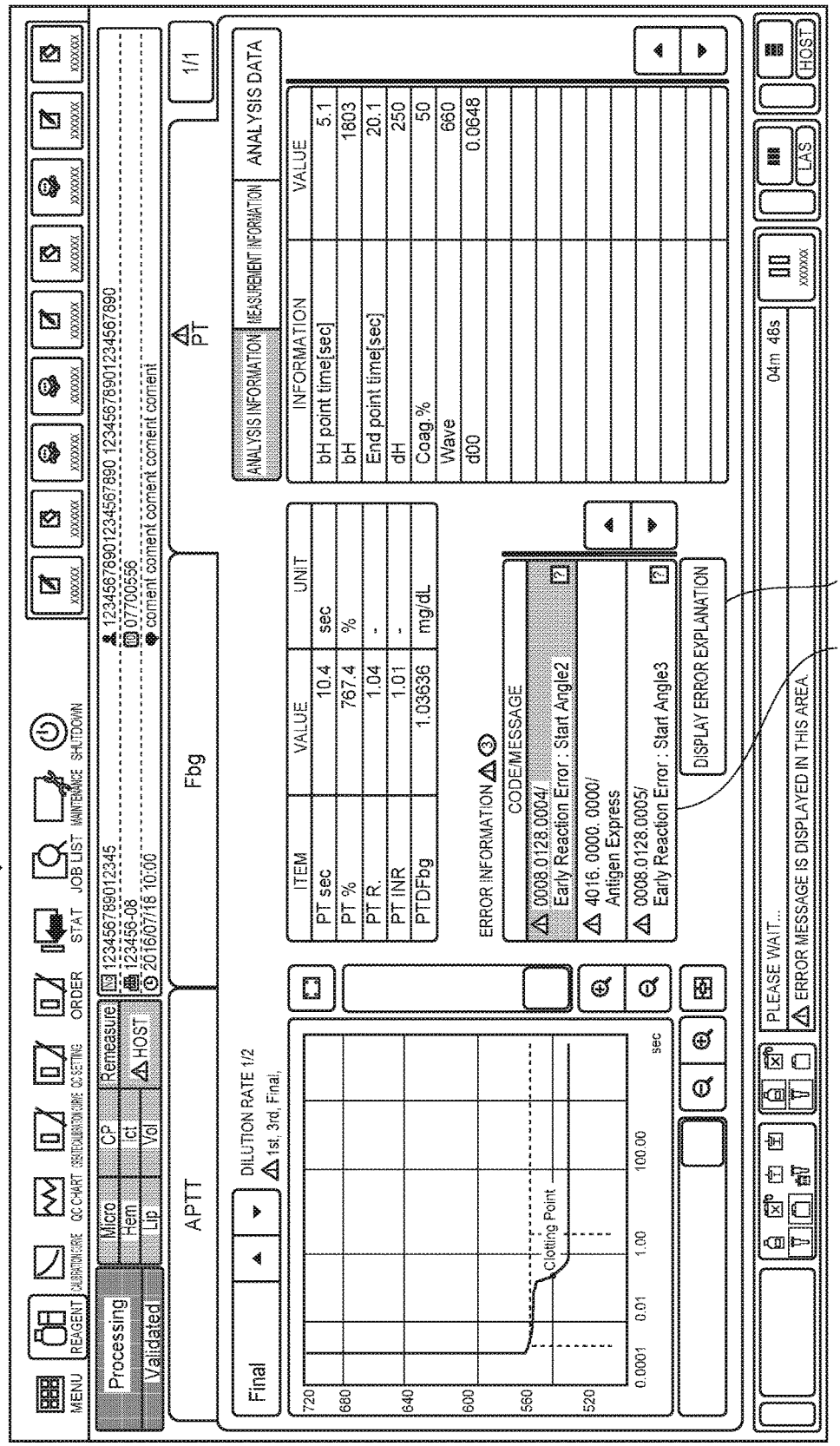

In FIG. 11C, when the screen is transitioned to the measurement result of PT, information on the error is displayed in the error information display region 750. The operator learns what kind of error has occurred by referring to this information. The operator touches the error explanation display button 760 to seek further information.

Figure 11D:

In FIG. 11D, the error explanation display region 780 is displayed on the same screen as the screen on which the measurement result of PT is displayed. The operator learns, referring to the explanation concerning the error and the measurement result of PT each other, a solution method that the operator should take. For example, the operator can determine whether to perform remeasurement using the same sample, perform remeasurement after applying specific treatment (centrifugal separation or the like) to the sample, or perform remeasurement after re-collecting a sample.

The invention includes other embodiments in addition to the above-described embodiments without departing from the spirit of the invention. Embodiments are to be considered in all respects as illustrative, and not restrictive. The scope of the invention is indicated by the appended claims rather than by the foregoing description. Hence, all configurations including the meaning and range within equivalent arrangements of the claims are intended to be embraced in the invention.

The invention claimed is:

1. A display method of displaying measurement results of measurement items obtained from a sample by a sample analyzer, the sample analyzer performing measurements for blood coagulation analysis, the method comprising:

determining, for each of the measurement items having respective ones of the measurement results obtained from the sample, whether an error is present in a measurement, wherein the measurement items comprise measurement items of the blood coagulation analysis, the measurement result includes a reaction curve in blood coagulation and the error is a reaction error in the blood coagulation;

displaying, on a display unit, selectable tabs on each of which a name of a single measurement item is displayed, in response to transitioning to a measurement result display screen that displays the measurement results only for the sample from a screen on which a sample display list is displayed such that, during display of the measurement result display screen, the screen on which the sample display list is displayed is not viewable, and displaying, on the display unit, an error notification mark on the selectable tab corresponding to the single measurement item in response to determining a presence of the reaction error for the single measurement item; and in response to selection, on the measurement result display screen for the sample, of selectable tab on which the error notification mark is displayed, displaying, on the display unit, a name of the reaction error and the measurement result including the reaction curve for the single measurement item for which the presence of the reaction error has been determined.

2. The display method according to claim 1, wherein the measurement result displayed comprises a graph related to the measurement result.

3. The display method according to claim 2, wherein the graph comprises a graph generated from the measurement result.

4. The display method according to claim 3, wherein the graph comprises a coagulation waveform.

5. The display method according to claim 3, wherein the graph comprises a calibration curve.

6. The display method according to claim 1, wherein the error notification mark comprises an error notification mark for calling attention of an operator of the sample analyzer.

7. The display method according to claim 1, wherein the displaying the selectable tabs comprises displaying the selectable tabs on which the names of the measurement items measured for the sample in a list on the display unit.

8. The display method according to claim 1, further comprising detecting an error of the measurement result of each of the measurement items.

9. The display method according to claim 1, wherein the displaying the error notification mark comprises displaying the error notification mark in a form according to a type of the error notification mark.

10. The display method according to claim 1, further comprising:
    displaying the tab on which the error notification mark is displayed at a
    predetermined position on the display unit.

11. A sample analyzer that performs measurements for blood coagulation analysis and displays measurement results of measurement items obtained from a sample, the sample analyzer comprising:
    a controller; and
    a display unit, wherein
    the controller determines, for each of the measurement items having respective ones of the measurement results obtained from the sample, whether an error is present in a measurement, wherein the measurement items comprise measurement items of the blood coagulation analysis, the measurement result includes a reaction curve in blood coagulation and the error is a reaction error in the blood coagulation;
    the controller displays, on a display unit, selectable tabs on each of which a name of a single measurement item is displayed, in response to transitioning to a measurement result display screen that displays the measurement results only for the sample from a screen on which a sample display list is displayed such that, during display of the measurement result display screen, the screen on which the sample display list is displayed is not viewable, and, displays, on the display unit, an error notification mark on the selectable tab corresponding to the single measurement item in response to determining a presence of the reaction error for the single measurement item; and
    the controller, in response to selection, on the measurement result display screen for the sample, of one selectable tab on which the error notification mark is displayed, displays, on the display unit, a name of the reaction error and the measurement result including the reaction curve for the single measurement item for which the presence of the reaction error has been determined.

12. A non-transitory computer-readable storage medium storing a computer program executable by a computer to perform operations comprising:
    determining, for each of measurement items obtained from a sample by a sample analyzer configured to perform measurements for blood coagulation analysis, whether an error is present in a measurement, wherein the measurement items comprise measurement items of the blood coagulation analysis, the measurement result includes a reaction curve in blood coagulation and the error is a reaction error in the blood coagulation;
    displaying, on a display unit, selectable tabs on each of which a name of a single measurement item is displayed, in response to transitioning to a measurement result display screen that displays the measurement results only for the sample from a screen on which a sample display list is displayed such that, during display of the measurement result display screen, the screen on which the sample display list is displayed is not viewable, and displaying, on the display unit, an error notification mark on the selectable tab corresponding to the single measurement item in response to determining a presence of the reaction error for the single measurement item; and
    in response to selection, on the measurement result display screen for the sample, of one selectable tab on which the error notification mark is displayed, displaying, on the display unit, a name of the reaction error and the measurement result including the reaction curve for the names of the single measurement item for which the presence of the reaction error has been determined.

\* \* \* \* \*

UNITED STATES PATENT AND TRADEMARK OFFICE
CERTIFICATE OF CORRECTION

| | | |
|---|---|---|
| PATENT NO. | : 12,241,904 B2 | |
| APPLICATION NO. | : 16/581808 | |
| DATED | : March 4, 2025 | |
| INVENTOR(S) | : Kazuma Moriura, Hiroshi Kurono and Akihito Kato | |

It is certified that error appears in the above-identified patent and that said Letters Patent is hereby corrected as shown below:

On the Title Page

Item (73) Assignee should read:
SYSMEX CORPORATION, Kobe (JP)

Signed and Sealed this
Eighth Day of April, 2025

Coke Morgan Stewart
*Acting Director of the United States Patent and Trademark Office*